US008664233B2

(12) United States Patent
Reichelt et al.

(10) Patent No.: US 8,664,233 B2
(45) Date of Patent: Mar. 4, 2014

(54) SUBSTITUTED 5H-PYRIMIDO[5,4-B]INDOLES, METHOD FOR THE PRODUCTION THEREOF AND USE THEREOF FOR TREATING NON-SOLID MALIGNANT TUMORS OF THE BLOOD-PRODUCING SYSTEM

(75) Inventors: Claudia Reichelt, Leipzig (DE);
Alexander Schulze, Bad Liebenwerda (DE); Mohammed Daghish, Leipzig (DE); Friedrich-Alexander Ludwig, Leipzig (DE); Jochen Heinicke, Leipzig (DE); Konrad Herrmann, Grimma (DE); Maj Schuster, Leipzig (DE); Sven Letschert, Leipzig (DE); Kenneth Mugridge, Leipzig (DE); Joseph DeAngelo, Chapel Hill, NC (US)

(73) Assignee: The Medicines Company (Leipzig) GmbH, Leipzig (DE)

( * ) Notice: Subject to any disclaimer, the term of this patent is extended or adjusted under 35 U.S.C. 154(b) by 845 days.

(21) Appl. No.: 12/520,480

(22) PCT Filed: Dec. 21, 2007

(86) PCT No.: PCT/EP2007/011387
§ 371 (c)(1),
(2), (4) Date: Jan. 20, 2010

(87) PCT Pub. No.: WO2008/077631
PCT Pub. Date: Jul. 3, 2008

(65) Prior Publication Data
US 2011/0021511 A1  Jan. 27, 2011

(30) Foreign Application Priority Data
Dec. 22, 2006  (DE) .......................... 10 2006 062 203

(51) Int. Cl.
*A01N 43/54* (2006.01)
*A61K 31/505* (2006.01)
*A01N 43/38* (2006.01)
*A61K 31/40* (2006.01)

(52) U.S. Cl.
USPC .......................... 514/267; 514/411; 544/251

(58) Field of Classification Search
USPC ................... 514/267, 411; 544/251
See application file for complete search history.

(56) References Cited

U.S. PATENT DOCUMENTS 6,608,053 B2 *  8/2003  Hayakawa et al. ........ 514/227.8

FOREIGN PATENT DOCUMENTS

| JP | 06220059 A | * | 8/1994 |
| WO | WO 03051884 A1 | * | 6/2003 |

OTHER PUBLICATIONS

Merino et al. "Synthesis and anti-HIV-1 activities of new pyrimido[5,4b]indoles" Il Farmaco, 1999, vol. 54, pp. 255-264.*
Morissette et al. "High-throughput crystallization: polymorphs, slats, co-crystals and solvates of pharmaceutical solids" Advanced Drug Delivery Reviews, 2004, vol. 56, pp. 275-300.*
Lotsch et al. "Misestimating the role of an active metabolite when modeling the effects after administration of teh parent compound only", Jul. 2006, Clinical Pharmacology & Therapeutics, pp. 95-97.*
Merino, I. et al., "Synthesis and anti-HIV-1 activities of new pyrimido[5,4-b]indoles", "Il Farmaco", Apr. 30, 1999, pp. 255264, vol. 54, No. 4 (Abstract Only Provided).

* cited by examiner

*Primary Examiner* — Kendra D Carter
(74) *Attorney, Agent, or Firm* — Hultquist PLLC; Steven J. Hultquist; Mary B. Grant

(57) ABSTRACT

The invention relates to compounds of general formula 1

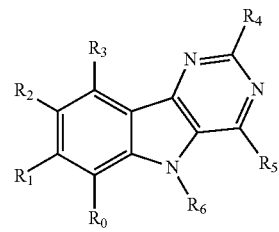

to processes for the production thereof, to pharmaceutical preparations containing said compounds and/or physiologically compatible salts and/or solvates which can be produced therefrom as well as to the pharmaceutical use of said compounds, the salts or solvates thereof as inductors of apoptosis in the case of non-solid malignant tumors of the hematopoietic system, in particular in the case of leukemias and lymphomas, more particularly in the case of leukemic B lymphocytes.

7 Claims, 2 Drawing Sheets

SUBSTITUTED 5H-PYRIMIDO[5,4-B]INDOLES, METHOD FOR THE PRODUCTION THEREOF AND USE THEREOF FOR TREATING NON-SOLID MALIGNANT TUMORS OF THE BLOOD-PRODUCING SYSTEM

CROSS-REFERENCE TO RELATED APPLICATIONS

This application is a U.S. national phase under the provisions of 35 USC §371 of International Application No. PCT/EP07/11387 filed Dec. 21, 2007 and published Jul. 3, 2008 as WO 2008/077631, which in turn claims priority of German Patent Application No. 10 2006 062 203 filed Dec. 22, 2006. The disclosures of such international application and German priority application are hereby incorporated herein by reference in their respective entireties, for all purposes.

The invention relates to derivatives of general formula 1

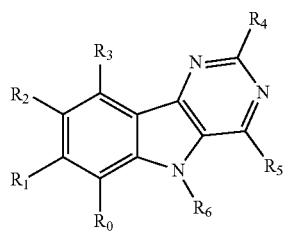

to processes for the production thereof, to pharmaceutical preparations containing said compounds and/or physiologically compatible salts and/or solvates which can be produced therefrom as well as to the pharmaceutical use of said compounds, the salts or solvates thereof as inductors of apoptosis in the case of non-solid malignant tumors of the hematopoietic system, in particular in the case of leukemias and lymphomas, more particularly in the case of leukemic B lymphocytes.

Non-solid malignant tumors of the hematopoietic system have become a more and more frequently occurring cancer disease in the industrial nations in the past decade. Progressing environmental pollution, smoking, exposure to contaminants and exposure to radiation (e.g. caused by the ozone hole or by nuclear power plants) are regarded as possible inductors.

The non-solid malignant tumors of the hematopoietic system comprise lymphomas and all possible forms of leukemia. While acute lymphatic leukemia (ALL) usually affects children and young adults, chronic lymphatic leukemia of B lymphocytes (B-CLL) is with about 30% of all cases is the most frequent form of leukemia of older people in the industrial nations. The average age is 65 years. Men are affected two times more often than women.

The most important basis for the treatment of cancer diseases of the hematopoietic system is and will be chemotherapy. However, the plurality of leukemias and lymphomas includes some forms which can be treated more successfully than others. This is e.g. leukemia in children or the non-Hodgkin lymphoma. Here, healing chances have already exceeded the 50% limit, in particular in the case of an early diagnosis. However, if chemotherapy of these tumors fails, they are often aggressive so as to cause death within some months. On the contrary, although the clinical course of B-CLL is usually less aggressive, this disease cannot be cured by established therapies and is fatal within 7 years on the average. However, about 10% of the B-CLL patients additionally develop a B-CLL transformation into an aggressive lymphoma in the course of the disease. Here, the average survival time following conventional chemotherapy is only about 6 months. This shows that the tumors of the hematopoietic system are not static and differentiated with respect to one another but represent a group of diseases which have some aspects in common. B-CLL is described in more detail below. However, the findings obtained substantially also apply to the other non-solid malignant tumors of the hematopoietic system.

Chronic lymphatic B cell type (B-CLL) leukemia is characterized by a progressive malignant accumulation of small $CD5^+$, $CD19^+$, $CD23^+$ B-CLL cells in the peripheral blood, in the bone marrow and in the secondary lymphatic organs. Although the peripheral B-CLL cells in the G0/early G1 phase of the cell cycle are arrested, proliferating leukemic B cells are also described which occur as pseudofollicles in what is called proliferation centers in lymph nodes and bone marrow. These proliferatively active cells seem to be of significance for the progression of the disease. These cells can be regarded as both the starting point for further relapses of leukemia and continuously fill the pool of the peripheral B-CLL cells.

The apparent expansion and accumulation of the malignant B lymphocytes in the case of CLL is substantially due to a disturbed apoptosis regulation of these cells. B-CLL cells express large amounts of the anti-apoptotic proteins Bcl2 and $Bclx_L$. On the contrary, only small amounts of the propapoptotic proteins Bax and $Bcl-x_s$ are synthesized. As a result, the balance of pro- and antiapoptotic signals shifts towards anti-apoptosis.

From the clinical point of view, a generalized lymphadenopathy, a hematomegaly and/or splenomegaly, fever, night sweat and weight loss stand out. In a developed stage of the disease there is an increased susceptibility to infections as a result of the displacement of the immunocompetent cells. Since the B-CLL cells are immunoincompetent, the patients develop a hypogammaglobulinemia which is one of the main causes for the susceptibility to infections. Autoimmune phenomena can be observed in about 20% of the patients. The risk of a second neoplasia is significantly increased.

In order to estimate the prognosis of B-CLL, the clinical stages as classified by Binet et al. (Cancer 48, 1981, pp. 198-206) or Rai et al. (Blood 46, 1975, pp. 219-234) are used. Recently, the diagnosis of genetic modifications in B-CLL could be improved decisively. As a result, it is possible to obtain additional prognostic information irrespective of the clinical stage.

In molecular genetic investigations, it was possible to identify two prognostically different B-CLL groups. In one group, it is possible to detect somatic mutations of the immunoglobulin chain (mutated Ig VH genes) which do not occur in the other group. The latter group shows a less favourable disease course and a faster progress of the disease as compared to the group with mutations. It has also been found that the increased expression of the surface antigen CD38 on B-CLL lymphocytes is significantly correlated with a poor prognosis of the disease. Recently, another prognostic marker could be identified, i.e. the zetta-associated protein (ZAB-70), which is also correlated with an unfavourable course of disease. Increased serum thymidine kinase, increased $\beta_2$ microglobulin and increased lactate dehydrogenase (LDH) are found as further clinical-chemical parameters in the case of B-CLL.

Today's standard therapy of B-CLL is palliative and is mainly carried out with the cytostatic agent chlorambucil or fludarabine. When relapses occur, a combination therapy using fludarabine, cyclophosphamide in combination with rituximab (monoclonal antibody against CD20) or campath (monoclonal antibody against CD52) is often initiated. The campath antibody recognizes, and binds to, the cell surface antigen CD52 which is expressed on healthy and also neoplastic B and T lymphocytes, monocytes and macrophages. After binding, the cells are lysed so as to inhibit the uncontrolled lymphocyte proliferation. Since only about 5% of the CD52 antigen is found on granulocytes and not on erythrocytes, thrombocytes and stem cells, they largely remain undamaged. However, along with the leukemic lymphocytes normal B and T lymphocytes are also damaged. This unintended toxic damage of healthy cells also manifests itself in a partially severe side-effect profile in this therapy.

The most frequent undesired side-effects of a campath therapy are: lymphopenia (100%); chill (89%); fever (83%); neutropenia (70%); thrombocytopenia (52%); nausea (47%); anemia (47%); opportunistic infections (43%); vomiting (33%); hypotension (15%); exanthema (30%); fatigue, weakness (22%); urticaria (22%); dyspnea (17%); sepsis (15%); itching (14%); headache (13%); and diarrhea (13%).

The illustrated severe side-effect profile shows that in spite of a good therapeutic effect monoclonal antibodies induce serious side effects.

Today's first-line standard therapy of B-CLL is the chemotherapy with the purine analog fludarabine (Fludara®) either as a monotherapy or as a combination therapy. In clinical studies, fludarabine shows significantly higher remission rates (60% versus 40%) and prolonged survival times (1300/1000 days) in CLL patients as compared to the formerly common combination scheme of cyclophosphamide, adriamycin and prednisolone (CAP).

As compared to campath, the side-effect profile of fludarabine is less marked, yet still has to be considered relevant. A granulocytopenia also usually occurs in this therapy form. Special care has to be taken when autoimmune phenomena occur after the administration of fludarabine. The occurrence of autoimmune-hemolytic anemias, thrombopenias and erythroblastopenias is frequently observed in patients after this therapy.

Recently, the role of the tumor suppressor gene p53 as a main inductor of apoptosis in tumor cells becomes the focus of scientific interest. The protein encoded by p53 binds as a transcription factor to the DNA, thus initiating the synthesis of further regulatory proteins which via an arrest of the cell cycle stop the cell division or also contribute to the fact that the cell is subject to apoptosis. Here, genes of the Bcl family are also activated which, in turn, activate the signal cascade of caspases, thus leading to apoptosis. In over 50% of human tumors, a mutation of the p53 gene can be shown, which clearly shows that such a defective p53 gene product can no longer initiate apoptosis, thus supporting the growth and the dividing capacity of tumor cells.

Mutations of the tumor suppressor gene p53 can be detected in about 10% of the patients suffering from B-CLL. Mutations in the p53 gene were also found in patients having other tumors of the hematopoietic system. In animal models, mutations in the p53 gene are accompanied by a poorer response to chemotherapies and irradiation. A correlation of the p53 mutations with clinical data showed that these p53 mutations predominantly occurred in patients who had received a therapy with alkylating agents (chorambucil, cyclophosphamide) on account of another cancer disease, for example. This correlation also proves that an apoptosis induction by alkylating agents, irradiation and by fludarabine is disturbed in p53 mutated patients. This analysis proves for the first time that a preceding therapy with alkylating agents is associated with the occurrence of p53 mutations in tumors of the hematopoietic system.

All medicaments approved of to date for the treatment of tumors of the hematopoietic system have drawbacks, as pointed out above, and in particular show lymphopenia, chill, fever, neutropenia, emesis and the like.

The causes of the drawbacks differ, yet can be based on a fundamental insufficiency of the medicaments used. This insufficiency is due to the fact that the active substances cannot adequately differentiate between the malignant leukemia cells and the vital other (blood) cells. This is because the reaction paths of the active substances are not sufficiently clear. Hence the medicaments induce or select mutations in tumor suppressor genes thus triggering resistances and also attack non-leukemic, i.e. healthy, blood cells and also cells of different origin.

Tricyclic type (1) compounds unsubstituted at the benzo ring ($R_0=R_1=R_2=R_3=H$) have been described on various occasions in the literature (cf. in this connection Chemical Abstracts Services, Registry, STN and other databases).

The objective of the invention is to provide novel and more effective compounds having a small side-effect profile for the treatment of patients suffering from non-solid malignant tumors of the hematopoietic system, in particular of patients suffering from chronic lymphatic leukemia.

It is the object of this invention to develop medicaments which efficiently induce apoptosis in the tumor cells and damage other healthy (blood) cells considerably less or not at all.

According to the invention, this object is achieved by producing and characterizing active substances which correspond to general formula 1.

DESCRIPTION OF THE INVENTION

The invention relates to compounds of general formula

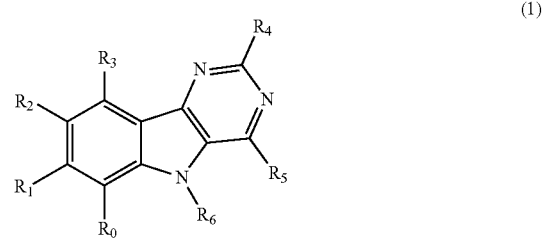

(1)

in which:
$R_0$, $R_1$ and $R_2$ are
  $L_A$-A-$L_B$-B in which:
  $L_A$ is:
    single bond,
    $NR^\#$, O, S, S(O), S(O)$_2$, S(O)$_2$—O, O—S(O)$_2$, —CHR$^\S$, —CH$_2$—O—, —CH$_2$—CH$_2$—O—, —O—CH$_2$, —O—CH$_2$—CH$_2$—, C=O
  A is:
    hydrogen
    $C_{1-6}$ alkyl (substituted, where appropriate, with $R^\S$),
    $C_{2-6}$ alkenyl (substituted, where appropriate, with $R^\S$),
    $C_{2-6}$ alkynyl (substituted, where appropriate, with $R^\S$),
    chlorine, bromine, iodine,
    azido, hydrazino, phenyl, substituted, where appropriate, once, twice or thrice with residues $R^§$ independently selected from one another, a monocyclic or bicyclic, saturated or monounsaturated or polyunsaturated heterocycle having 4-14 ring atoms, among them 1-5 heteroatoms (preferably N, O, S) which may be substituted, where appropriate, once, twice or thrice with residues Fe independently selected from one another and/or one or several oxygen atoms, and, in case A cannot be substituted any further, $L_B$ and B are irrelevant, $L_A$-A and $L_A$-A-$L_B$ may jointly also be a single bond in each case, $L_B$ is:
single bond
$NR^\#$, O, S, S(O), $S(O)_2$, $S(O)_2$—O, O—$S(O)_2$, —$CHR^§$, —$CH_2$—O—, —$CH_2$—$CH_2$—O, —O—$CH_2$, —O—$CH_2$—$CH_2$—, C=O, the following functional groups B is:
hydrogen
alkyl, substituted, where appropriate, with $R^§$,
$C_{2-6}$ alkenyl (substituted, where appropriate, with $R^§$),
$C_{2-6}$ alkynyl (substituted, where appropriate, with $R^§$),
arylalkyl- with $C_{6-12}$ aryl and $C_{1-5}$ alkyl (alkyl and/or aryl substituted, where appropriate, with $R^§$),
alkyl, monosubstituted or polysubstituted with monocyclic or bicyclic, saturated or monounsaturated or polyunsaturated heterocycles having 4-14 ring atoms among them 1-5 heteroatoms (preferably N, O, S), which may be substituted, where appropriate, once, twice or thrice with residues $R^§$ independently selected from one another and/or one or more oxygen atoms, aryl, in particular phenyl substituted, where appropriate, with $R^§$ a monocyclic or bicyclic, saturated or monounsaturated or polyunsaturated heterocycle having 4-14 ring atoms among them 1-5 heteroatoms (preferably N, O, S) which, where appropriate, may be substituted once, twice or thrice with residues $R^§$ independently selected from one another and/or one or more oxygen atoms, $R^\#$
hydrogen, alkyl (substituted, where appropriate, with $R^§$)

$R_3$ is
hydrogen,
$C_{1-6}$ alkyl, straight-chain, branched or $C_{3-6}$ alkyl also cyclic as well as substituted, where appropriate, once, twice or thrice with residues $R^§$ independently selected from one another, $R^§$
$C_{1-6}$ alkoxy, straight-chain, branched or $C_{3-6}$ alkoxy also cyclic as well as substituted, where appropriate, once, twice or thrice with residues $R^§$ independently selected from one another, a monocyclic, saturated or monounsaturated or polyunsaturated heterocycle having 4-8 ring atoms among them 1-3 heteroatoms, preferably N, O and S, $R_4$ is
$NR_7R_8$, in which this substituent is on the whole:
morpholino, thiomorpholino, thiomorpholino-S,S-dioxide, pyrrolidino, piperidino, 1-piperazinyl, 1-homopiperazinyl, 4-$C_{1-6}$ alkyl piperazin-1-yl, 4-aryl-1-piperzin-1-yl, 4-Bn-piperazin-1-yl (substituted, where appropriate, with $R^§$ at the heterocycloaliphatic ring),
further amino residues of secondary, monocyclic or polycyclic amines having a total of 4-14 ring atoms, including the representatives substituted on the C skeleton with $R^§$ $C$-$L_c$, in which:
C is:
$NR^\#$, O, S, S(O), $S(O)_2$, $S(O)_2$—O, O—$S(O)_2$, —O—$CH_2$, —O—$CH_2$—$CH_2$—, C=O, C(O)O—, single bond $L_c$ is:
$C_{1-6}$ alkyl (substituted, where appropriate, with $R^§$)
$C_{2-6}$ alkenyl (substituted, where appropriate, with $R^§$),
$C_{2-6}$ alkynyl (substituted, where appropriate, with $R^§$),
fluorine, chlorine, bromine, iodine,
CN, SCN
azido, hydrazino,
phenyl substituted, where appropriate, with $R^§$,
a monocyclic or bicyclic, saturated or monounsaturated or polyunsaturated heterocycle having 4-14 ring atoms among them 1-5 heteroatoms (preferably N, O, S), which may be substituted, where appropriate, with a residue $R^§$ and/or one or several oxygen atoms, $R^\#$ is
hydrogen, alkyl (substituted, where appropriate, with $R^§$)

$R_5$ is
  monocyclic, bicyclic or tricyclic, saturated or monounsaturated or polyunsaturated heterocyclic residue having a total of 4-14 ring atoms, among them 1-5 heteroatoms (preferably N, O and S) substituted, where appropriate, with $R^§$,
  $C_{1-6}$ alkyl, $C_{1-6}$ alkoxy, $C_{1-6}$ alkylthio, $C_{1-6}$alkylamino, $C_{1-6}$ dialkylamino, each straight-chain, branched or cyclic and substituted, where appropriate, with $R^§$ with the exception of $NH(CH_2)_2N(CH_3)_2$, $NH(CH_2)_3N(CH_3)_2$ and $NH(CH_2)_2N(C_2H_5)_2$
  a saturated or monounsaturated or polyunsaturated heterocyclic residue bound via an exocyclic atom selected from group O, N, S and having a total of 4-10 ring atoms among them 1-5 heteroatoms (preferably N, O and S), substituted, where appropriate, with $R^5$,
  a saturated or monounsaturated or polyunsaturated heterocyclic residue which is bound via an atom bound at the tricycle and selected from group O, N or S and a downstream $C_{1-6}$ alkylene group and which has a total of 4-10 ring atoms among them 1-5 heteroatoms (preferably N, O and S), substituted, where appropriate, with $R^§$,
  hydroxy, halogen (Cl, Br, I)
$R_6$ is
  hydrogen
  $C_{1-6}$ alkyl, straight-chain, branched or $C_{3-6}$ alkyl also cyclic as well as substituted, where appropriate, once, twice or thrice with residues $R^§$ selected independently from one another
  $C_{2-6}$ alkenyl (substituted, where appropriate, with $R^§$)
  alkyl substituted once or several times with monocyclic or bicyclic saturated or monounsaturated or polyunsaturated heterocycles having 4-14 ring atoms among them 1-5 heteroatoms which are preferably N, O and S that may carry one or several oxygen atoms at C, N and/or S and, where appropriate, are substituted once, twice or thrice with residues $R^§$ independently selected from one another, as well as substituted, where appropriate, with $R^§$,
  carbonyl or sulfonyl, each substituted with
    hydrogen, $C_{1-6}$ alkyl (substituted, where appropriate, with $R^§$)
    $C_{2-6}$ alkenyl (substituted, where appropriate, with $R^§$)
    $C_{2-6}$ alkynyl (substituted, where appropriate, with $R^§$)
    aryl, in particular phenyl (substituted, where appropriate, with $R^§$)
    a monocyclic or bicyclic, saturated or monounsaturated or polyunsaturated heterocycle having 4-14 ring atoms among them 1-5 heteroatoms (preferably N, O and S) which may be substituted, where appropriate, once, twice or thrice with residues $R^§$ independently selected from one another and/or one or more oxygen atoms,
$R^§$
  OH, —SH, —O—$C_{1-8}$ alkyl, —O—$C_{6-14}$ aryl, —S—$C_{1-4}$ alkyl, —S—$C_{6-14}$ aryl, —SO—$C_{1-4}$ alkyl, —SO—$C_{6-14}$ aryl, —$SO_2$—$C_{1-4}$ alkyl, —$SO_2$—$C_{6-14}$ aryl, —$SO_3H$, —$OSO_2C_{1-8}$ alkyl, —$OSO_2C_{6-14}$ aryl, —COOH, —COO$C_{1-8}$ alkyl, —(CO)$C_{1-8}$ alkyl,
  COOH, —$CONH_2$, —CONH$C_{1-6}$ alkyl, —CON($C_{1-6}$ alkyl)$_2$, —$NH_2$, —NH$C_{1-6}$ alkyl, —N($C_{1-6}$ alkyl)$_2$, —NH$C_{6-14}$ aryl, —NH-hetaryl, —N($C_{6-14}$ aryl)$_2$, —N($C_{1-6}$ alkyl)($C_{6-14}$ aryl),
  $C_{1-6}$ alkyl, —$C_{2-12}$ alkenyl, —$C_{2-12}$ alkynyl, each straight-chain, branched or cyclic as well as substituted, where appropriate, once, twice or thrice with halogen independently of one another,
  halogen (—F, —Cl, —Br, —I)
  $CH_2CH_2OH$, —$CH_2CH_2SH$, —$CH_2CH_2SCH_3$,
  sulfamoyl, alkyl sulfamoyl, dialkyl sulfamoyl with alkyl $C_{1-5}$ substituted, where appropriate, with methoxy,
  amidino, hydroxyamidino
  sulfo, phosphono,
  —CN, —$NO_2$ and —SCN
as well as pharmaceutically compatible salts, solvates, active metabolites, tautomers and prodrugs of these compounds, with compounds wherein

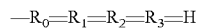

being excluded.

The terms "alkyl, alkenyl, alkynyl, alkoxy, etc.", also in word combinations such as alkyl sulfonyl, alkylamino or alkoxycarbonyl, etc., designate both the unbranched and branched possible compounds. Likewise, "alkenyl and alkynyl" refer to the correspondingly possible monounsaturated or polyunsaturated compounds. The same also applies to the corresponding cyclic compounds.

"Aryl" refers to an aromatic monocyclic or polycyclic ring system having 6 to 14 carbon atoms, preferably 6 to 10 carbon atoms. The aryl group can be substituted, where appropriate, with one or several ring substituents. Preferred aryl groups are phenyl or naphthyl.

"Halogen" means fluorine, chlorine, bromine or iodine.

"Monocyclic or bicyclic, saturated or monounsaturated or polyunsaturated heterocycles having 5-14 ring atoms among them 1-5 heteroatoms which are preferably N, O and S, substituted, where appropriate, once, twice or thrice with residues $R^§$ independently selected from one another" preferably comprise the following groups:
thienyl, pyridinyl, pyrimidinyl, piperazinyl, pyridyl, isoxazolyl, piperidinyl, pyrazinyl, morpholino, pyrrolyl, triazinyl, tetrazolyl, oxazolyl, benzo[d][1,3]dioxolyl, indolyl, imidazolyl, pyrazolyl, furanyl.

"Heteroaryl" (sometimes referred to as "hetaryl") denotes an aromatic monocyclic or polycyclic ring system having 5 to 14 ring atoms, preferably 5 to 10 ring atoms, where 1 or more ring atoms are an element other than carbon, e.g. N, O or S, as such or in combination. Preferred hetaryls contain 5 or 6 ring atoms. The hetaryls may be substituted, where appropriate, at one or more ring systems. Examples of suitable hetaryls are: pyridyl, pyrazinyl, pyridinyl, furanyl, thienyl, pyrimidinyl, isoxazolyl, isothiazolyl, oxazolyl, thiazolyl, pyrazolyl, furazanyl, pyrrolyl, triazolyl, 1,2,4-thiadiazolyl, pyrazinyl, pyridazinyl, benzofurazanyl, indolyl, azaindolyl, benzoimidazolyl, benzothienyl, quinolinyl, imidazolyl, thienopyridinyl, 1,2,4-triazinyl, benzothiazolyl or benzoazaindolyl.

In the sense of the invention, all residues are considered combinable with one another unless stated otherwise in the definition of the residues. All conceivable subgroups thereof shall be considered disclosed.

The invention also relates to physiologically compatible salts of the compounds of general formula (1). The physiologically compatible salts are obtained as usual by reaction of basic compounds of general formula (1) with inorganic or organic acids, where appropriate, also in the presence of compounds having acidic properties, when e.g. one of the substituents $R^1$, $R^2$, $R^3$ or $R^4$ is —COOOH or —$SO_3H$ in said compounds, by neutralization with inorganic or organic bases.

Hydrochloric acid, sulphuric acid, nitric acid or hydrobromic acid are preferably used as inorganic acids and e.g. formic acid, acetic acid, propionic acid, glycolic acid, lactic acid, amygdalic acid, tartaric acid, malic acid, citric acid, malonic acid, maleic acid, fumaric acid, succinic acid, alginic acid, benzoic acid, 2-, 3- and 4-alkyloxy and acyloxy benzoic acids, ascorbic acid, $C_1$-$C_3$ alkylsulfonic acids, benzenesulfonic acid, nicotinic acid, isonicotinic acid and amino acids are used as organic acids.

For example, ammonia, soda lye and caustic potash solution are used as inorganic bases and alkylamines, $C_1$-$C_3$ pyridine, quinoline, isoquinoline, piperazine and derivatives thereof, and picolines, quinaldine or pyrimidine are used as organic bases.

In addition, physiologically compatible salts of the compounds according to general formula (1) can be obtained by converting the substances which as substituents have a tertiary amino group, can be converted in basically known manner with alkylating agents—such as alkyl or aralkyl halides—into the corresponding quaternary ammonium salts.

The invention also relates to solvates of the compounds, including the pharmaceutically acceptable salts, acids, bases and esters as well as the active metabolites thereof and, where appropriate, the tautomers thereof according to general formula (1) including prodrug formulations. Prodrug formulations here comprise all substances which are formed by simple transformation including hydrolysis, oxidation or reduction either enzymatically, metabolically or in any other way. A suitable prodrug contains e.g. a substance of general formula (1) bound via an enzymatically cleavable linker (e.g. carbamate, phosphate, N-glycoside or a disulfide group) to a dissolution-improving substance (e.g. tetraethylene glycol, saccharides, formic acids or glucuronic acid, etc.). Such a prodrug of a compound according to the invention can be applied to a patient, and this prodrug can be transformed into a substance of general formula (1) so as to obtain the desired pharmacological effect.

The compounds according to the invention can be administered in different ways, e.g. orally, parenterally, cutaneously, subcutaneously, intravenously, intramuscularly, rectally, or by inhalation. The intravenous administration or administration by inhalation is preferred. The compound is given to a patient who needs a therapy for a disease coming under the indication spectrum of the compounds according to the invention over a period to be determined by a physician. The compound can be administered to both humans and other mammals.

The dosage of the compounds according to the invention is determined by the physician on the basis of the patient-specific parameters, such as age, weight, sex, severity of the disease, etc. The dosage is preferably from 0.001 mg/kg to 1000 mg/kg body weight, preferably from 0.01 to 500 mg/kg body weight and most preferably from 0.1 to 100 mg/kg body weight.

Corresponding to the kind of administration, the medicament is suitably formulated, e.g. in the form of solutions or suspensions, simple tablets or dragees, hard or soft gelatine capsules, suppositories, ovules, preparations for injection, which are prepared according to common galenic methods.

The compounds according to the invention can be formulated, where appropriate, together with further active substances and with excipients common in pharmaceutical compositions, e.g.—depending on the preparation to be produced—talcum, gum arabic, lactose, starch, magnesium stearate, cocoa butter, aqueous and non-aqueous carriers, fatty bodies of animal or vegetable origin, paraffin derivatives, glycols (in particular polyethylene glycol), various plasticizers, dispersants or emulsifiers, pharmaceutically compatible gases (e.g. air, oxygen, carbon dioxide, etc.), preservatives.

In order to produce liquid preparations, additives, such as sodium chloride solution, ethanol, sorbitol, glycerine, olive oil, almond oil, propylene glycol or ethylene glycol, can be used.

When solutions for infusion or injection are used, they are preferably aqueous solutions or suspensions, it being possible to produce them prior to use, e.g. from lyophilized preparations which contain the active substance as such or together with a carrier, such as mannitol, lactose, glucose, albumin and the like. The ready made solutions are sterilized and, where appropriate, mixed with excipients, e.g. with preservatives, stabilizers, emulsifiers, solubilizers, buffers and/or salts for regulating the osmotic pressure. The sterilization can be obtained by sterile filtration using filters having a small pore size according to which the composition can be lyophilized, where appropriate. Small amounts of antibiotics can also be added to ensure the maintenance of sterility.

Furthermore, inhalation compositions, e.g. in the form of aerosols, sprays or as micronized powder, are preferably produced. For this purpose, the compounds according to the invention are either dissolved or suspended in pharmaceutically conventional solvents and finely divided by means of excess pressure in a certain volume and inhaled. The procedure is made correspondingly in the solid substances to be inhaled which are also finely divided by means of excess pressure and inhaled. Other applicators working by means of excess pressure are also included here.

The invention also relates to pharmaceutical preparations which contain a therapeutically active amount of the active ingredients (compound according to the invention of formula (I)) together with organic or inorganic solid or liquid, pharmaceutically compatible carriers which are suited for the intended administration and which interact with the active ingredients without drawbacks:

Preferred substances according to the invention are:
7-bromo-4-ethoxy-9-fluoro-2-(piperazin-1-yl)-5H-pyrimido [5,4-b]indole
7-bromo-2-chloro-4-ethoxy-9-(piperazin-1-yl)-5H-pyrimido[5,4-b]indole
7-bromo-4-ethoxy-2-(piperazin-1-yl)-5H-pyrimido[5,4-b] indol-9-ol
4-ethoxy-2-(piperazin-1-yl)-7-(pyridin-4-yl)-5H-pyrimido [5,4-b]indol-9-ol
4-ethoxy-7-(3,4-dimethoxyphenyl)-2-(piperazin-1-yl)-5H-pyrimido[5,4-b]indol-9-ol
7-(3,4-dimethoxyphenyl)-2-(piperazin-1-yl)-5H-pyrimido [5,4-b]indole-4,9-diol
4-ethoxy-8-(3,4,5-trimethoxyphenyl)-2-(piperazin-1-yl)-5H-pyrimido[5,4-b]indole
1-(7-(3,4-dimethoxyphenyl)-2-(piperazin-1-yl)-5H-pyrimido[5,4-b]indol-4-yl)piperidin-4-ol
7-(3,4-dimethoxyphenyl)-2-(piperazin-1-yl)-5H-pyrimido [5,4-b]indol-4-ol
4-((pyridin-2-yl)methoxy)-7-(3,4-dimethoxyphenyl)-2-(piperazin-1-yl)-5H-pyrimido[5,4-b]indole
4-((pyridin-4-yl)methoxy)-7-(3,4-dimethoxyphenyl)-2-(piperazin-1-yl)-5H-pyrimido[5,4-b]indole
4-((pyridin-3-yl)methoxy)-7-(3,4-dimethoxyphenyl)-2-(piperazin-1-yl)-5H-pyrimido[5,4-b]indole
4-methylthio-2-(piperazin-1-yl)-7-(pyridin-4-yl)-5H-pyrimido[5,4-b]indole
2-(7-(3,4-dimethoxyphenyl)-2-(piperazin-1-yl)-5H-pyrimido[5,4-b]indol-4-ylamino)ethanol
7-bromo-2-(piperazin-1-yl)-5H-pyrimido[5,4-b]indol-4-ol
4-(2-morpholinoethoxy)-7-(3,4-dimethoxyphenyl)-2-(piperazin-1-yl)-5H-pyrimido[5,4-b]indole 7-(3,4-dimethoxyphenyl)-4-morpholino-2-(piperazin-1-yl)-5H-pyrimido[5,4-b]indole 7-(3,4-dimethoxyphenyl)-2-(piperazin-1-yl)-4-thiomorpholino-5H-pyrimido[5,4-b]indole 4-morpholino-2-(piperazin-1-yl)-7-(pyrindin-4-yl)-5H-pyrimido[5,4-b]indole 7-(3,4-dimethoxyphenyl)-N-(2-morpholinoethyl)-2-(piperazin-1-yl)-5H-pyrimido[5,4-b]indole-4-amine 7-(3,4-dimethoxyphenyl)-2-(piperazin-1-yl)-4-piperidino-5H-pyrimido[5,4-b]indole 4-cyclopropylmethoxy-7-(3,4-dimethoxyphenyl)-2-(piperazin-1-yl)-5H-pyrimido[5,4-b]indole 4-(1H-imidazol-1-yl)-7-(3,4-dimethoxyphenyl)-2-(piperazin-1-yl)-5H-pyrimido[5,4-b]indole 7-(3,4-dimethoxyphenyl)-2-(piperazin-1-yl)-4-(piperidin-4-yloxy)-5H-pyrimido[5,4-b]indole 4-cyclopropylmethoxy-2-(piperazin-1-yl)-7-(pyridin-4-yl)-5H-pyrimido[5,4-b]indole 4-ethoxy-2-morpholino-7-(pyridin-4-yl)-5H-pyrimido[5,4-b]indole 4-(4-ethoxy-2-(piperazin-1-yl)-5H-pyrimido[5,4-b]indol-7-yl)benzoic acid ethyl ester 4-(4-ethoxy-2-(piperazin-1-yl)-5H-pyrimido[5,4-b]indol-7-yl)benzoic acid hydrochloride 4-(4-ethoxy-2-(piperazin-1-yl)-5H-pyrimido[5,4-b]indol-7-yl)phenol hydrochloride 3-(4-ethoxy-2-(piperazin-1-yl)-5H-pyrimido[5,4-b]indol-7-yl)benzoic acid methyl ester 3-(4-ethoxy-2-(piperazin-1-yl)-5H-pyrimido[5,4-b]indol-7-yl)benzoic acid hydrochloride 4-ethoxy-7-(furan-2-yl)-2-(piperazin-1-yl)-5H-pyrimido[5,4-b]indole tert-butyl-2-(4-ethoxy-2-(piperazin-1-yl)-5H-pyrimido[5,4-b]indol-7-yl)-1H-pyrrole-1-carboxylate tert-butyl-4-(4-ethoxy-7-(pyridin-3-yl)-5H-pyrimido[5,4-b]indol-2-yl)-piperazine-1-carboxylate 7-(benzo[d][1,3]dioxol-5-yl)-4-ethoxy-2-(piperazin-1-yl)-5H-pyrimido[5,4-b]indole 7-(3,4-dimethoxyphenyl)-2-(piperazin-1-yl)-N-(thiazol-2-yl)-5H-pyrimido[5,4-b]indole-4-amine 7-(3,4-dimethoxyphenyl)-2-(piperazin-1-yl)-4-(1H-pyrrol-1-yl)-5H-pyrimido[5,4-b]indole 7-(3,4-dimethoxyphenyl)-2-(piperazin-1-yl)-4-(1H-pyrazol-1-yl)-5H-pyrimido[5,4-b]indole 7-(3,4-dimethoxyphenyl)-2-(piperazin-1-yl)-4-(1H-1,2,3-triazol-1-yl)-5H-pyrimido[5,4-b]indole 7-(3,4-dimethoxyphenyl)-2-(piperazin-1-yl)-4-(4H-1,2,4-triazol-4-yl)-5H-pyrimido[5,4-b]indole 7-(3,4-dimethoxyphenyl)-2-(piperazin-1-yl)-4-(pyrrolidin-1-yl)-5H-pyrimido[5,4-b]indole (4-(4-ethoxy-2-(piperazin-1-yl)-5H-pyrimido[5,4-b]indol-7-yl)piperazin-1-yl)(phenyl)methanone 4-ethoxy-2-(piperazin-1-yl)-7-(4-(pyrimidin-2-yl)piperazin-1-yl)-5H-pyrimido[5,4-b]indole 4-ethoxy-2-(piperidin-4-yl)-7-(pyridin-4-yl)-5H-pyrimido[5,4-b]indole 4-ethoxy-7-(3,4-dimethoxyphenyl)-2-(piperidin-4-yl)-5H-pyrimido[5,4-b]indole 4-ethoxy-7-(3,4-dimethoxyphenyl)-2-(piperidin-3-yl)-5H-pyrimido[5,4-b]indole 4-ethoxy-7-(3,4-dimethoxyphenyl)-2-(pyridin-4-yl)-5H-pyrimido[5,4-b]indole 7-(3,4-dimethoxyphenyl)-2-(piperazin-1-yl)-5H-pyrimido[5,4-b]indol-4-ol N,N-di-(2-hydroxyethyl)-4-ethoxy-7-(pyridin-4-yl)-5H-pyrimido[5,4-b]indole-2-amine 2-(4-ethoxy-9-methoxy-2-(piperazin-1-yl)-5H-pyrimido[5,4-b]indol-7-yl)benzeneamine 2-{2-(piperazin-1-yl)-7-(pyridin-4-yl)-5H-pyrimido[5,4-b]indol-4-yloxy}ethanol 2-ethoxy-4-(piperazin-1-yl)-7-(pyridin-4-yl)-5H-pyrimido[5,4-b]indole 4-ethoxy-2-(4-methylpiperazin-1-yl)-7-(pyridin-4-yl)-5H-pyrimido[5,4-b]indole 4-ethoxy-2-(piperazin-1-yl)-6-(pyridin-4-yl)-5H-pyrimido[5,4-b]indole 4-ethoxy-2-(piperazin-1-yl)-7-(2-aminopyridin-5-yl)-5H-pyrimido[5,4-b]indole 4-ethoxy-2-(piperazin-1-yl)-7-(3,4-dimethoxy-phenyl)-5H-pyrimido[5,4-b]indole 4-ethoxy-2-(piperazin-1-yl)-7-(pyridin-3-yl)-5H-pyrimido[5,4-b]indole 4-ethoxy-2-(piperazin-1-yl)-7-(pyridin-4-yl)-5H-pyrimido[5,4-b]indole 4-ethoxy-2-(piperazin-1-yl)-8-(pyridin-4-yl)-5H-pyrimido[5,4-b]indole 4-ethoxy-7-morpholino-2-(piperazin-1-yl)-5H-pyrimido[5,4-b]indole 4-ethoxy-9-methoxy-2-(piperazin-1-yl)-7-(pyridin-4-yl)-5H-pyrimido[5,4-b]indole The following compounds are particularly preferred:

2-(4-ethoxy-9-methoxy-2-(piperazin-1-yl)-5H-pyrimido[5,4-b]indol-7-yl)benzeneamine 2-{2-(piperazin-1-yl)-7-(pyridin-4-yl)-5H-pyrimido[5,4-b]indol-4-yloxy}ethanol 2-ethoxy-4-(piperazin-1-yl)-7-(pyridin-4-yl)-5H-pyrimido[5,4-b]indole 4-ethoxy-2-(4-methylpiperazin-1-yl)-7-(pyridin-4-yl)-5H-pyrimido[5,4-b]indole 4-ethoxy-2-(piperazin-1-yl)-6-(pyridin-4-yl)-5H-pyrimido[5,4-b]indole 4-ethoxy-2-(piperazin-1-yl)-7-(2-aminopyridin-5-yl)-5H-pyrimido[5,4-b]indole 4-ethoxy-2-(piperazin-1-yl)-7-(3,4-dimethoxy-phenyl)-5H-pyrimido[5,4-b]indole 4-ethoxy-2-(piperazin-1-yl)-7-(pyridin-3-yl)-5H-pyrimido[5,4-b]indole 4-ethoxy-2-(piperazin-1-yl)-7-(pyridin-4-yl)-5H-pyrimido[5,4-b]indole 4-ethoxy-2-(piperazin-1-yl)-8-(pyridin-4-yl)-5H-pyrimido[5,4-b]indole 4-ethoxy-7-morpholino-2-(piperazin-1-yl)-5H-pyrimido[5,4-b]indole 4-ethoxy-9-methoxy-2-(piperazin-1-yl)-7-(pyridin-4-yl)-5H-pyrimido[5,4-b]indole 4-(4-ethoxy-2-(piperazin-1-yl)-5H-pyrimido[5,4-b]indol-7-yl)benzoic acid ethyl ester 4-(4-ethoxy-2-(piperazin-1-yl)-5H-pyrimido[5,4-b]indol-7-yl)benzoic acid hydrochloride 4-(4-ethoxy-2-(piperazin-1-yl)-5H-pyrimido[5,4-b]indol-7-yl)phenol hydrochloride 3-(4-ethoxy-2-(piperazin-1-yl)-5H-pyrimido[5,4-b]indol-7-yl)benzoic acid methyl ester 3-(4-ethoxy-2-(piperazin-1-yl)-5H-pyrimido[5,4-b]indol-7-yl)benzoic acid hydrochloride The compound 4-ethoxy-2-(piperazin-1-yl)-7-(pyridin-4-yl)-5H-pyrimido[5,4-b]indole is particularly preferred.

The invention also relates to processes for producing pharmaceutical preparations which are characterized in that the compound according to the invention is mixed with a pharmaceutically compatible carrier.

The compounds according to the invention are also suited for combination therapies with previously known active substances for the treatment of the above mentioned diseases. In this connection, surprising synergy effects are to be used to increase the therapeutic effectiveness of the substances according to the invention. The combination may be, on the one hand, to offer a single pharmaceutical composition which contains at least one of the compounds according to the invention in combination with one or more of the below active substances or several preparations which contain one or more of the below active substances are administered to the patient simultaneously or time-staggered with respect to the pharmaceutical composition according to the invention.

It is preferred to combine one or more of the compounds according to the invention with one or more of the following active substances:

nucleoside analogues (e.g. fludarabine, cladribine)
alkylating agents (e.g. chlorambucil, cyclophosphamide)
$\beta_2$ adrenoceptor agonists (e.g. terbutaline, salbutanol, salmetanol, fenoterole, formoterole)
disodium cromoglycate
corticosteroids
leukotriene antagonists (either enzyme inhibitors [such as 5-lipoxygenase inhibitors or arachidonic acid enzyme inhibitors] or receptor antagonists), e.g. pramkulaste, montelukaste, zafirlukast, zileuton
antihistamines (preferably those having mast cell-stabilizing properties or leukotriene-antagonizing aspects, such as loratadine, astemizole, mizolastine, olopatadine theophylline
broad-spectrum inhibitors of phosphodiesterases
inhibitors of phosphodiesterases 3, 4 and 7
muscarine receptor antagonists, e.g. spiriva
(monoclonal) antibodies against TNF-alpha or other active substances which inhibit the formation or release of TNF-alpha or the activity of TNF-alpha (e.g. recombinant soluble receptor constructs)
(monoclonal) antibodies (e.g. rituximab, TACl-Ig)

The combination with nucleoside analogues, alkylating agents, monoclonal antibodies, corticosteroids, PDE inhibitors, leukotriene antagonists, antihistamines, theophyline, muscarine receptor antagonists and/or TNF-alpha inhibitors particularly serves for decelerating the acute disease state to be treated since the compounds according to the invention and the other active substances positively influence complementary aspects of the pathophysiological mechanisms underlying the disease. According to the invention in particular the combination of the compounds according to the invention with nucleoside analogues or alkylating agents, PDE inhibitors and glucocorticoids should result in synergistic effects regarding the triggering of an apoptosis of the leukemic B cells. Such a synergistic effect could be observed in a combination with fludarabine, for example (see examples). In combination with glucocorticoids, a positive effect is that less glucocorticoids have to be used so as to achieve a saving effect and the side effects known from glucocorticoids are reduced or fully lack.

Depending on the development of the disease and the underlying symptoms, the ratio between the compounds according to the invention and the other active substances in combination can be 1:10,000 to 10,000:1, preferably 1:1,000 to 1,000:1, most preferably 1:10 to 10:1.

As to the substances according to the invention dose-effect curves were established using the program Sigma Plot, and the $EC_{50}/IC_{50}$ values for every substance were calculated on the basis of these progress charts. The $IC_{50}$ values for the substances according to the invention are between 0.1 and 5 µM.

Applicant has found that the apoptosis inducing effect of the substances according to the invention on purified B lymphocytes from patients suffering from leukemia was subject to an individual variation width. Among the patients there were groups responding strongly, moderately or rather weakly to the active substances according to the invention. However, a cytotoxicity on leukemic cells was found in every case. Applicant then discovered in investigations that the leukemic B lymphocytes of B-CLL patients with an 11q deletion responded in a particularly sensitive way to the apoptosis inducing effect of the substances according to the invention. Therefore, they are a particularly preferred group of patients and also show the best treatment results.

Applicant has also investigated whether the substances according to the invention trigger apoptosis in healthy B lymphocytes, which might have a negative effect on the side-effect profile thereof. It has been found that the substances according to the invention influence B-CLL cells having an $EC_{50}$ of $1.83 \pm 0.95$ µM about sixteen times more than healthy PBMC cells having an $EC_{50}$ of $29.49 \pm 13.4$ µM. Thus, it has been possible to show free of doubt that the substances according to the invention have a very good therapeutic effect on leukemia cells without affecting the other healthy blood cells. The direct effective comparison of fludarabine as a current golden standard with the substances according to the invention in the blood of B-CLL patients shows an $EC_{50}$ value from 2 µM to 200 µM for fludarabine (literature and own values) while the substances according to the invention have $EC_{50}$ values from 10 nM to 5 µM.

Another advantageous property of the substances according to the invention is that in contrast to the positive control, i.e. saponine, human erythrocytes do not hemolyze.

In order to detect the specific induction of programmed cell death (apoptosis), a detection thereof was carried out by means of the caspase-3/7 activity; the caspase-3/7 activity is described in the literature as a safe evidence of apoptosis. It has been found that depending on the concentration the substances according to the invention activate the trigger enzymes decisive for apoptosis, i.e. caspases 3, 7 and 9. This found data clearly proves that the cell cytotoxicity caused by the substances according to the invention is no toxic effect resulting in the necrosis of cells but that it is an induction of apoptosis.

The invention also relates to processes for the production of the compounds according to the invention.

The processes according to the invention for the production of the compounds of general formula 1 with the above listed meanings of $R_0$, $R_1$, $R_2$, $R_3$, $R_4$, $R_5$ and $R_6$ are characterized by the following procedures:

General Presentation According to Scheme 1:

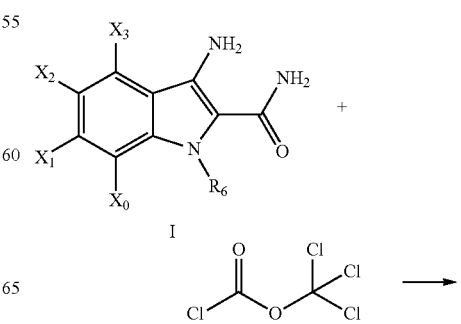

-continued

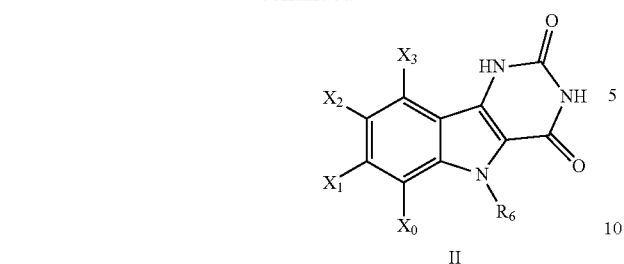

II

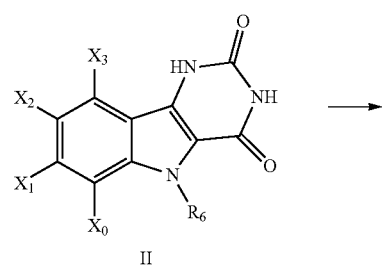

II

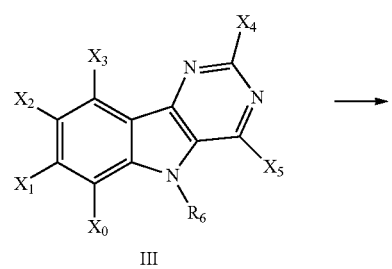

III

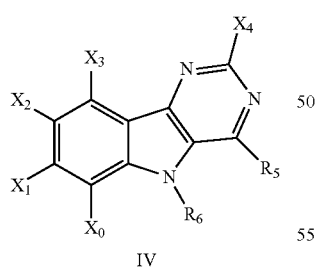

IV

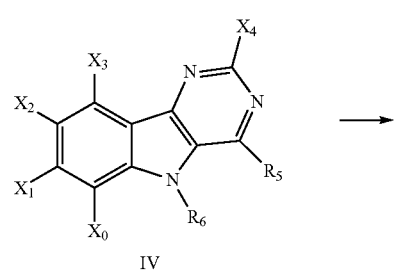

IV

-continued

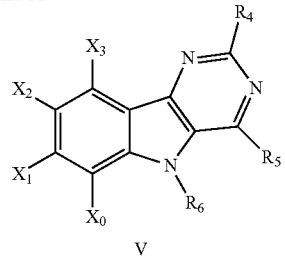

V

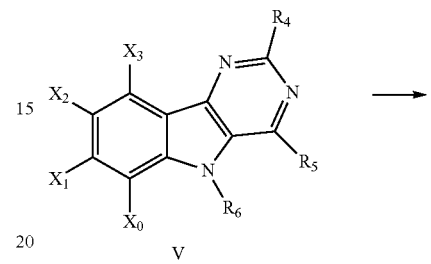

V

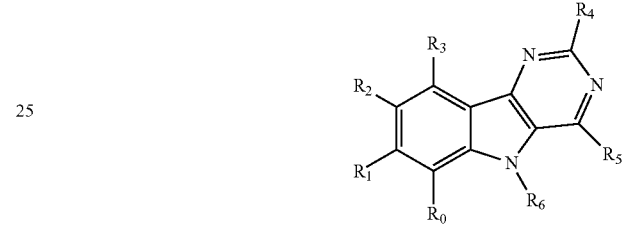

I $X_0$-$X_5$ = independently like or unlike F, Cl, Br, I, H, wherein $X_4$, $X_5$ unlike H Reaction of the compounds of general formula I with phosgene derivatives, preferably diphosgene, in a suitable solvent, preferably dioxan or toluene, to give the compounds of general formula II.

Reaction of the compounds of general formula II with a halogenating agent, preferably dichlorophenyl phosphine oxide, phosphorus trichloride, phosphorus pentachloride, phosphorus oxychloride or the mixtures thereof, each in the heat, to give the compounds of general formula III.

Reaction of the compounds of general formula III with O, N, S or C nucleophiles, preferably alcoholates, amines and thiolates, in alkanols or, where appropriate, aprotic, dipolar solvents while heating, in exceptional cases also at room temperature, to give the tricyclic compounds of general formula IV.

Reaction of the compounds of general formula IV with O, N, S or C nucleophiles, preferably alcoholates, amines and thiolates, in a suitable solvent, preferably toluene, mesitylene or dioxan while heating, in exceptional cases also at room temperature, to give the compounds of general formula V.

Reaction of the compounds of general formula V with O, N, S or C nucleophiles in a suitable solvent, preferably toluene, dioxan or THF, while heating and using suitable catalysts, in exceptional cases with the use of a microwave oven, to give the compounds of general formula 1.

Each of the residues $R_0$, $R_1$, $R_2$, $R_4$, $R_5$ and $R_6$ can be introduced in different synthesis stages by means of suitable reactions, in particular metal catalyzed C—C cross-coupling reactions, and, where appropriate, using suitable protecting groups or are already included in the corresponding educts.

EXAMPLES

Figure 1:
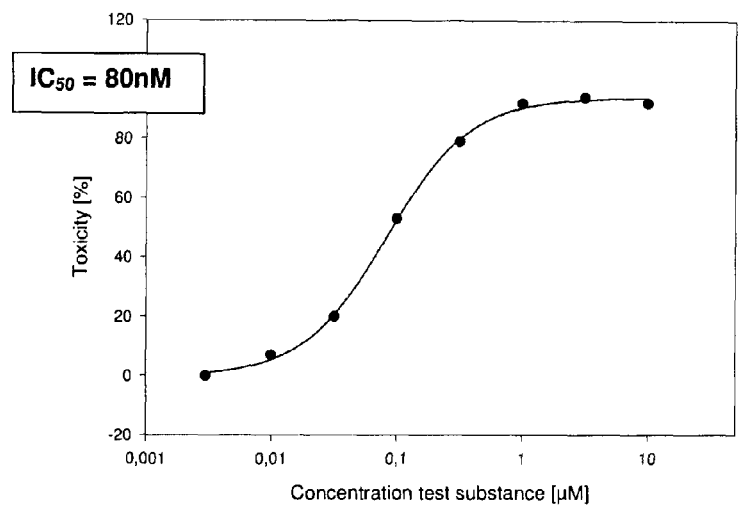
FIG. 1 is a graph of Toxicity (%) as a function of Concentration test substance (μM).

The invention is further described by means of the below examples.

Example 1

Synthesis of 2-(4-ethoxy-9-methoxy-2-(piperazin-1-yl)-5H-pyrimido[5,4-b]indol-7-yl)benzene amine

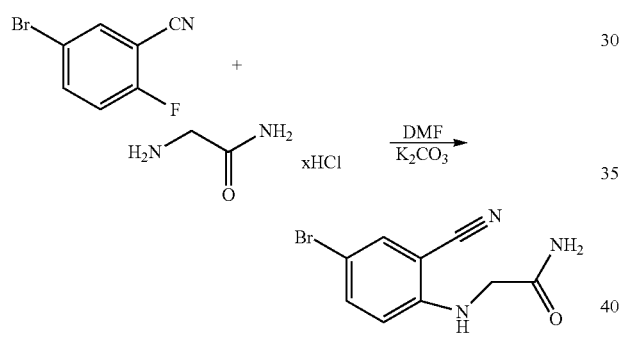

12.6 (58.3 mmol) 4-bromo-2,6-difluorobenzonitrile, 6.8 g (61.5 mmol) glycinamide hydrochloride and 16.1 g (116.5 mmol) $K_2CO_3$ were suspended in 50 ml DMF and heated at 70° C. for 18 h. Having cooled down to room temperature, the solvent was concentrated and water was added. The resulting precipitate was sucked off and washed with water. 13.3 g (84%) 2-(5-bromo-2-cyano-3-fluorophenylamino)acetamide was obtained. ESI-MS [m/z]: 272, 274 [M+H]$^+$

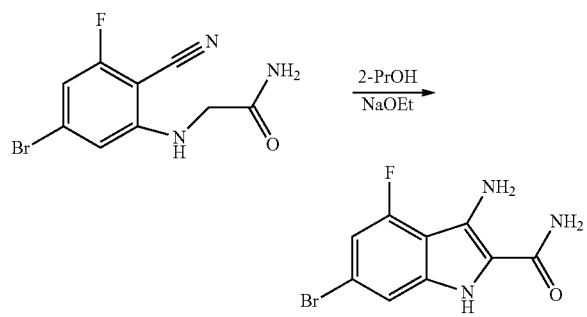

17.3 g (63.6 mmol) 2-(5-bromo-2-cyano-3-fluorophenylamino)acetamide was suspended in 150 ml 2-propanol and, after the addition of 10 ml NaOEt solution (21% in EtOH), the suspension was refluxed for 14 h. Having cooled down to room temperature, the solvent was concentrated and water was added. The resulting precipitate was sucked off and washed with water. 15.4 g (89%) 3-amino-6-bromo-4-fluoro-1H-indole-2-carboxylic acid amide was obtained. ESI-MS [m/z]: 272, 274 [M+H]$^+$

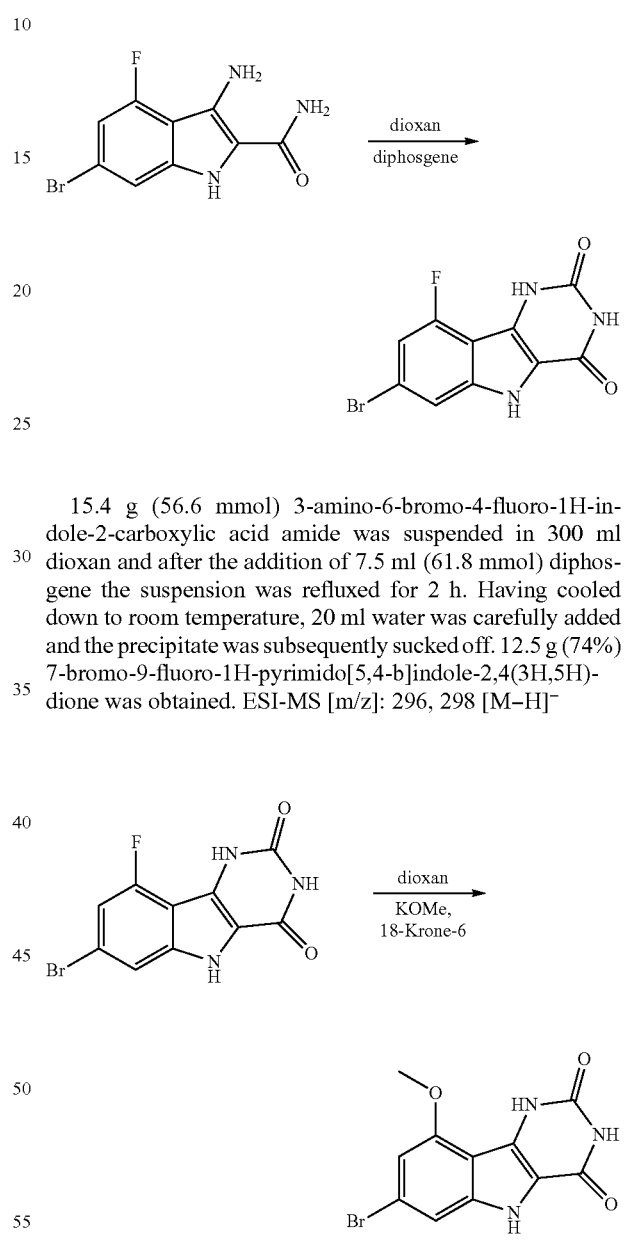

15.4 g (56.6 mmol) 3-amino-6-bromo-4-fluoro-1H-indole-2-carboxylic acid amide was suspended in 300 ml dioxan and after the addition of 7.5 ml (61.8 mmol) diphosgene the suspension was refluxed for 2 h. Having cooled down to room temperature, 20 ml water was carefully added and the precipitate was subsequently sucked off. 12.5 g (74%) 7-bromo-9-fluoro-1H-pyrimido[5,4-b]indole-2,4(3H,5H)-dione was obtained. ESI-MS [m/z]: 296, 298 [M−H]$^-$ 1.7 g (5.7 mmol) 7-bromo-9-fluoro-1H-pyrimido[5,4-b]indole-2,4(3H,5H)-dione, 4.5 g (17.0 mmol) 18-Krone-6 and 12 ml (162.5 mmol) 30% KOMe solution (MeOH) were refluxed in 600 ml dioxan for 20 h. Having cooled down to room temperature, the solvent was concentrated, water was added and acidified using 1 N HCl. The resulting precipitate was sucked off and washed with water. 650 mg (37%) 7-bromo-9-methoxy-1H-pyrimido[5,4-b]indole-2,4(3H, 5H)-dione was obtained. ESI-MS [m/z]: 308, 310 [M−H]$^-$

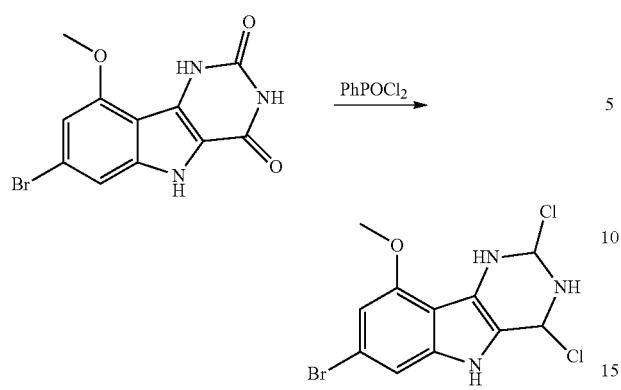
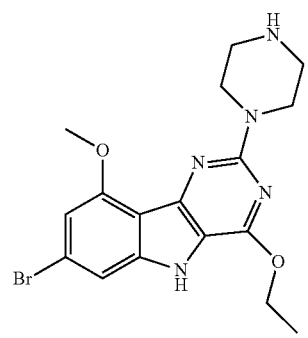

650 mg (2.1 mmol) 7-bromo-9-methoxy-1H-pyrimido[5,4-b]indole-2,4(3H,5H)-dione and 1.8 ml (12.6 mmol) dichlorophenyl phosphinoxide were heated to 185° C. for 6 h. Having cooled down to room temperature, the mixture was poured onto 40 g ice water and neutralized with saturated sodium hydrogen carbonate solution. The resulting precipitate was sucked off and washed with water. 600 mg (83%) 7-bromo-2,4-dichloro-9-methoxy-5H-pyrimido[5,4-b]indole was obtained. ESI-MS [m/z]: 344, 346, 348 [M−H]⁻

150 mg (0.42 mmol) 7-bromo-2-chloro-4-ethoxy-9-methoxy-5H-pyrimido[5,4-b]indole and 181 mg (2.1 mmol) piperazine were refluxed in 10 ml dioxan for 60 h. Then, the solvent was removed and the residue was suspended in water and sucked off. 130 mg (76%) 7-bromo-4-ethoxy-9-methoxy-2-(piperazin-1-yl)-5H-pyrimido[5,4-b]indole was obtained. ESI-MS [m/z]: 406, 408 [M+H]⁺

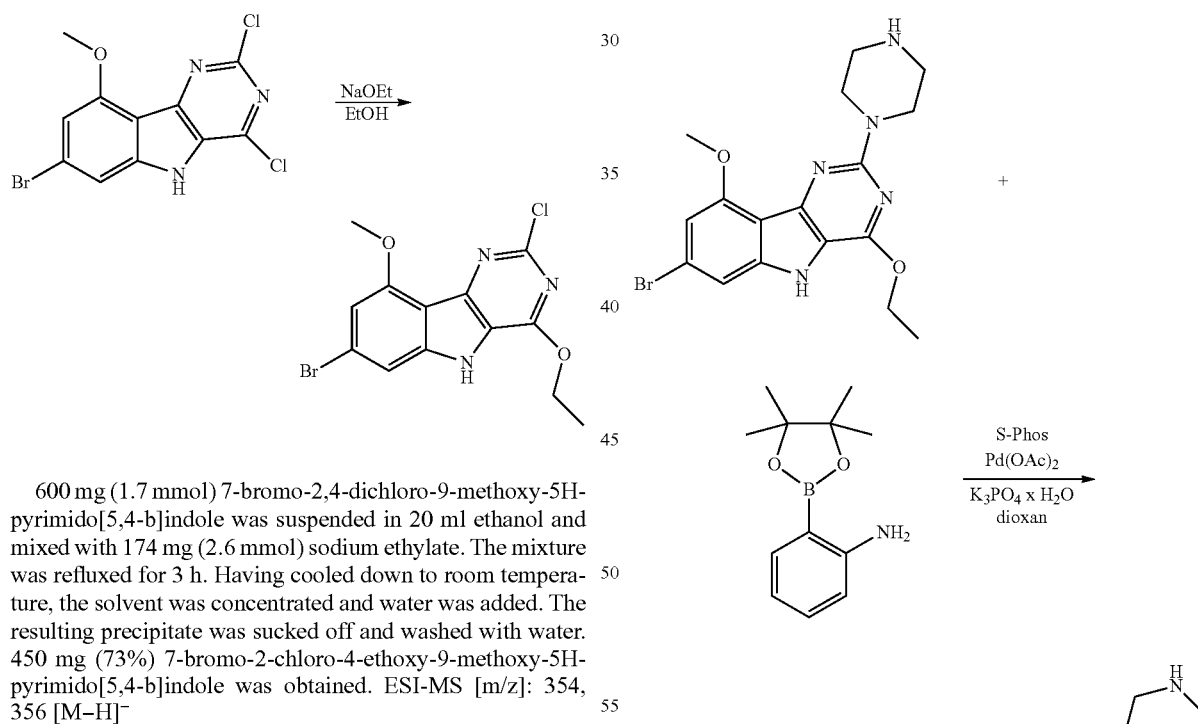

600 mg (1.7 mmol) 7-bromo-2,4-dichloro-9-methoxy-5H-pyrimido[5,4-b]indole was suspended in 20 ml ethanol and mixed with 174 mg (2.6 mmol) sodium ethylate. The mixture was refluxed for 3 h. Having cooled down to room temperature, the solvent was concentrated and water was added. The resulting precipitate was sucked off and washed with water. 450 mg (73%) 7-bromo-2-chloro-4-ethoxy-9-methoxy-5H-pyrimido[5,4-b]indole was obtained. ESI-MS [m/z]: 354, 356 [M−H]⁻

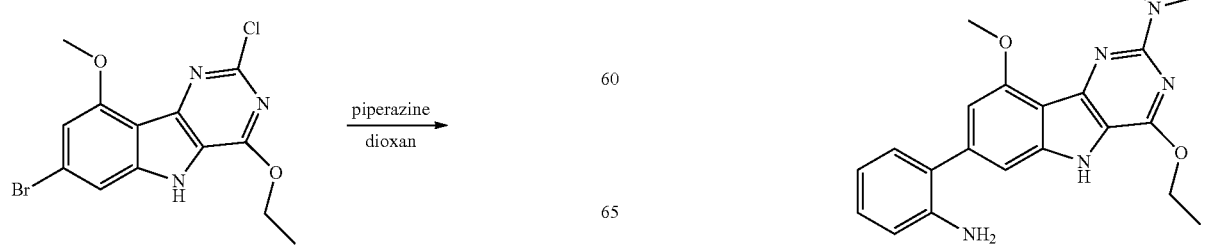

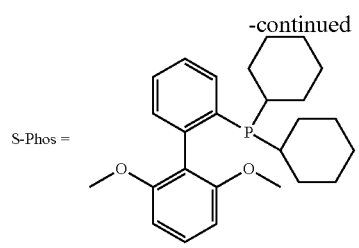

S-Phos =

70 mg (0.17 mmol) 7-bromo-4-ethoxy-9-methoxy-2-(piperazin-1-yl)-5H-pyrimido[5,4-b]indole, 56 mg (0.26 mmol) 2-(4,4,5,5-tetramethyl-1,3,2-dioxaborolan-2-yl)aniline, 119 mg (0.51 mmol) $K_3PO_4 \times H_2O$, 2.8 mg (6.8 μmol) S-Phos and 0.8 mg (3.4 μmol) $Pd(OAc)_2$ in 6 ml dioxan were heated in a microwave oven to 120° C. for 1 h. Then, the solvent was removed and after LC ($CH_2Cl_2$:MeOH, 0-20%) 20 mg (24%) of the title substance was obtained. ESI-MS [m/z]: 419 [M+H]$^+$ Example 2

Synthesis of 4-ethoxy-9-methoxy-2-(piperazin-1-yl)-7-(pyridin-4-yl)-5H-pyrimido[5,4-b]indole 60 mg (0.15 mmol) 7-bromo-4-ethoxy-9-methoxy-2-(piperazin-1-yl)-5H-pyrimido[5,4-b]indole (Example 1), 47 mg (0.23 mmol) 4-(4,4,5,5-tetramethyl-1,3,2-dioxaborolan-2-yl)pyridine, 61 mg (0.45 mmol) $K_2CO_3$, 2.4 mg (6.0 μmol) S-Phos and 0.7 mg (3.0 μmol) $Pd(OAc)_2$ in 6 ml dioxan were heated in a microwave oven to 120° C. for 1 h. Thereafter, the solvent was removed and following LC ($CH_2Cl_2$:MeOH, 0-30%) 27 mg (45%) of the title substance was obtained. ESI-MS [m/z]: 405 [M+H]$^+$ The following compounds were obtained in analogy to Examples 1 and 2 (Table 1)

TABLE 1

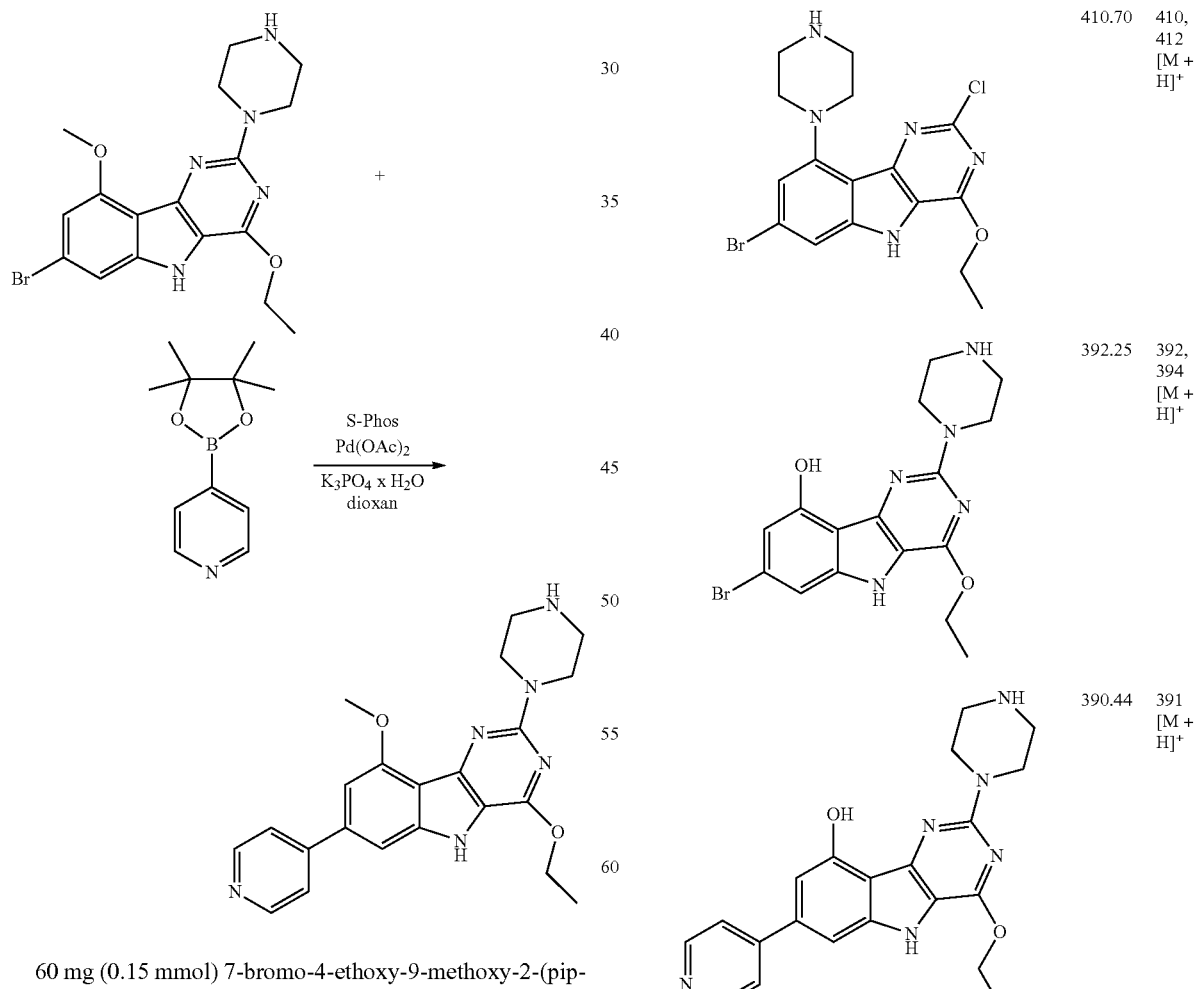

| Structure | M [g/mol] | ESI MS [m/z] |
|---|---|---|
| 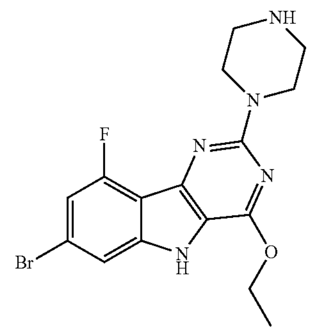 [SMILES: CCOc1nc(N2CCNCC2)nc2c1[nH]c1cc(Br)cc(F)c12] | 394.24 | 394, 396 [M + H]$^+$ |
| 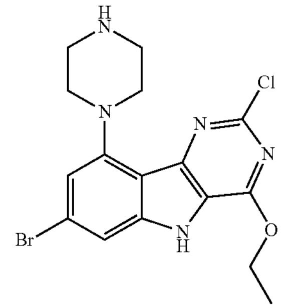 [SMILES: CCOc1nc(Cl)nc2c1[nH]c1cc(Br)cc(N3CCNCC3)c12] | 410.70 | 410, 412 [M + H]$^+$ |
| 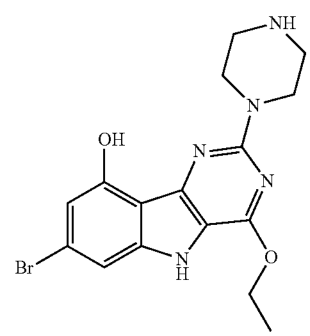 [SMILES: CCOc1nc(N2CCNCC2)nc2c1[nH]c1cc(Br)cc(O)c12] | 392.25 | 392, 394 [M + H]$^+$ |
| 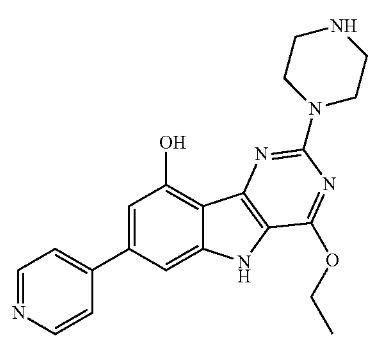 [SMILES: CCOc1nc(N2CCNCC2)nc2c1[nH]c1cc(-c3ccncc3)cc(O)c12] | 390.44 | 391 [M + H]$^+$ |

TABLE 1-continued

| Structure | M [g/mol] | ESI MS [m/z] |
|---|---|---|
| 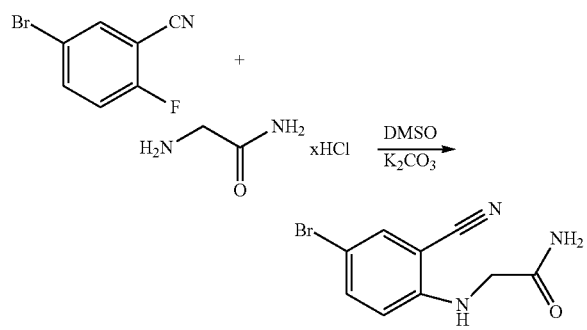 | 449.50 | 450 [M + H]+ |
| 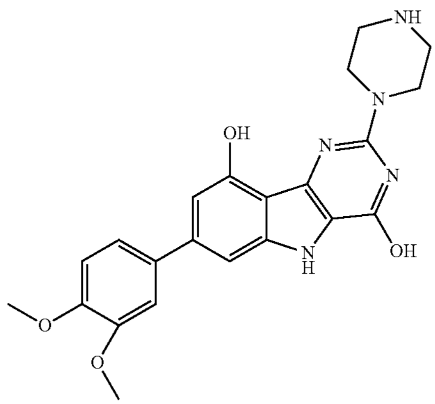 [SMILES: COc1ccc(-c2cc(O)c3c(c2)[nH]c2c(O)nc(N4CCNCC4)nc23)cc1OC] | 421.45 | 422 [M + H]+ |

Example 3

Synthesis of 4-ethoxy-2-(piperazin-1-yl)-8-(pyridin-4-yl)-5H-pyrimido[5,4-b]indole 16.3 g (81.5 mmol) 5-bromo-2-fluorobenzonitrile, 9.2 g (83.1 mmol) glycinamide hydrochloride and 23.6 g (170.8 mmol) K$_2$CO$_3$ were suspended in 40 ml DMSO and heated at 100° C. for 3 h. Having cooled down to room temperature, the solvent was concentrated and water was added. The resulting precipitate was sucked off and washed with water. 16.0 g (77%) 2-(4-bromo-2-cyano-phenylamino)acetamide was obtained. ESI-MS [m/z]: 254, 256 [M+H]+

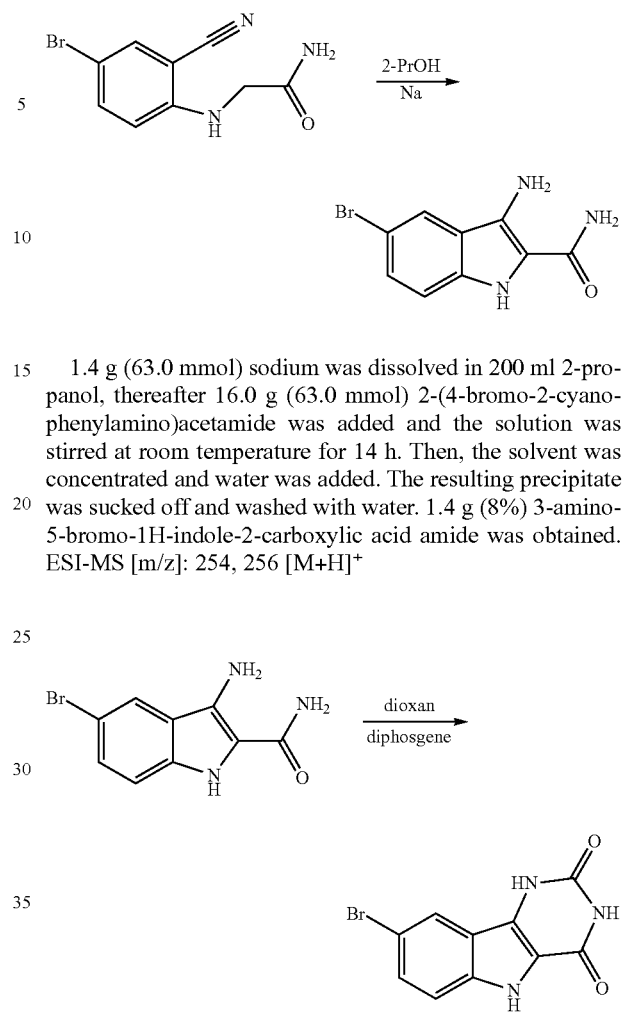

1.4 g (63.0 mmol) sodium was dissolved in 200 ml 2-propanol, thereafter 16.0 g (63.0 mmol) 2-(4-bromo-2-cyano-phenylamino)acetamide was added and the solution was stirred at room temperature for 14 h. Then, the solvent was concentrated and water was added. The resulting precipitate was sucked off and washed with water. 1.4 g (8%) 3-amino-5-bromo-1H-indole-2-carboxylic acid amide was obtained. ESI-MS [m/z]: 254, 256 [M+H]+

1.3 g (5.1 mmol) 3-amino-5-bromo-1H-indole-2-carboxylic acid amide was suspended in 50 ml dioxan and, after the addition of 670 µl (5.5 mmol) diphosgene, refluxed for 2 h. Having cooled down to room temperature, 2 ml water was carefully added and thereafter the precipitate was sucked off. 1.4 g (94%) 8-bromo-1H-pyrimido[5,4-b]indole-2,4(3H,5H)-dione was obtained. ESI-MS [m/z]: 278, 280 [M−H]−

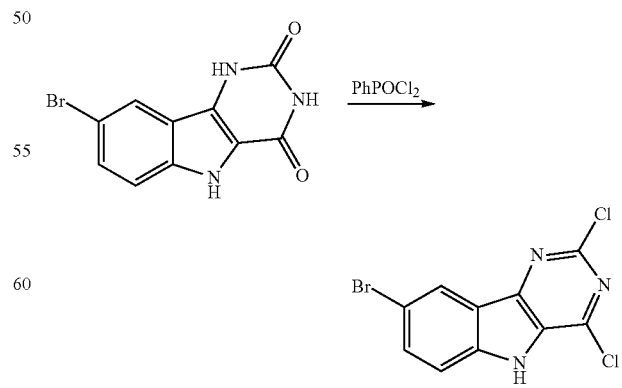

1.35 g (4.8 mmol) 8-bromo-1H-pyrimido[5,4-b]indole-2,4(3H,5H)-dione and 8 ml (57.4 mmol) dichlorophenyl phosphinoxide were heated to 180° C. for 6 h. Having cooled down to room temperature, the product was poured onto 40 g ice water and neutralized with saturated sodium hydrogen carbonate solution. The resulting precipitate was sucked off and washed with water. 930 mg (61%) 8-bromo-2,4-dichloro-5H-pyrimido[5,4-b]indole was obtained. ESI-MS [m/z]: 314, 316, 318 [M−H]⁻

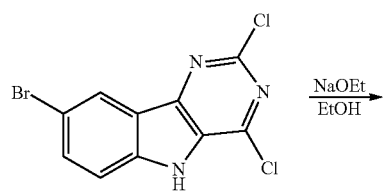

930 mg (2.9 mmol) 8-bromo-2,4-dichloro-5H-pyrimido[5,4-b]indole was suspended in 20 ml ethanol and mixed with 592 mg (8.7 mmol) sodium ethylate. The mixture was refluxed for 8 h. Having cooled down to room temperature, the solvent was concentrated and water was added. The resulting precipitate was sucked off and washed with water. 920 mg (97%) 8-bromo-2-chloro-4-ethoxy-5H-pyrimido[5,4-b]indole was obtained. ESI-MS [m/z]: 324, 326 [M−H]⁻

920 mg (2.9 mmol) 8-bromo-2-chloro-4-ethoxy-5H-pyrimido[5,4-b]indole and 813 mg (9.5 mmol) piperazine were heated in 10 ml mesitylene to 150° C. for 18 h. Then, the solvent was removed and the residue was suspended in water and sucked off. 650 mg (60%) 8-bromo-4-ethoxy-2-(piperazin-1-yl)-5H-pyrimido[5,4-b]indole was obtained. ESI-MS [m/z]: 376, 378 [M+H]⁺

100 mg (0.27 mmol) 8-bromo-4-ethoxy-2-(piperazin-1-yl)-5H-pyrimido[5,4-b]indole, 83 mg (0.41 mmol) 4-(4,4,5,5-tetramethyl-1,3,2-dioxaborolan-2-yl)pyridine, 344 mg (1.62 mmol) K₃PO₄×H₂O, 2.8 mg (6.8 µmol) S-Phos and 0.8 mg (3.4 µmol) Pd(OAc)₂ in 6 ml THF were heated in a microwave oven to 120° C. for 2 h. Thereafter, the solvent was removed and following purification by means of preparative HPLC (RP18) 52 mg (32%) of the title substance was obtained as double TFA salt. ESI-MS [m/z]: 375 [M+H]⁺

The following compounds were obtained in analogy to Example 3 (Table 2)

TABLE 2

| Structure | M [g/mol] | ESI MS [m/z] |
|---|---|---|
| 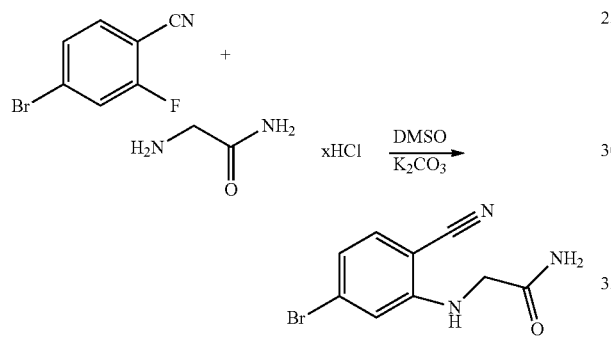 | 463.53 | 464 [M + H]+ |

Example 4

Synthesis of 7-bromo-4-ethoxy-2-(piperazin-1-yl)-5H-pyrimido[5,4-b]indole

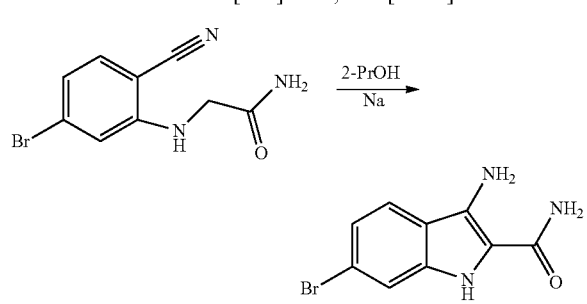

9.1 g (45.5 mmol) 4-bromo-2-fluorobenzonitrile, 10.0 g (91.0 mmol) glycinamide hydrochloride and 15.7 g (114 mmol) $K_2CO_3$ were suspended in 80 ml DMSO and heated at 120° C. for 5.5 h. Having cooled down to room temperature, the solvent was concentrated and water was added. The resulting precipitate was sucked off and washed with water. 11.6 g (100%) 2-(5-bromo-2-cyano-phenylamino)acetamide was obtained. ESI-MS [m/z]: 254, 256 [M+H]+

1.55 g (67.3 mmol) sodium was dissolved in 200 ml 2-propanol, then 14.3 g (56.1 mmol) 2-(5-bromo-2-cyano-phenylamino)acetamide was added and the solution was refluxed for 30 min. Thereafter, the reaction mixture was cooled down to 0° C. and saturated $NH_4Cl$ solution was added. The solvent was concentrated, the resulting precipitate was sucked off and washed with water. 12.2 g (86%) 3-amino-6-bromo-1H-indole-2-carboxylic acid amide was obtained. ESI-MS [m/z]: 254, 256 [M+H]+

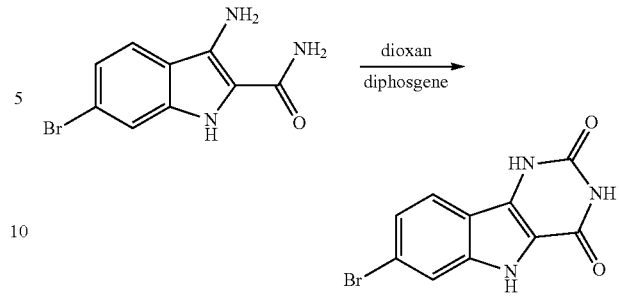

12.2 g (58 mmol) 3-amino-6-bromo-1H-indole-2-carboxylic acid amide was suspended in 50 ml dioxan, and, after the addition of 11.7 ml (96 mmol) diphosgene, the suspension was refluxed for 2 h. Having cooled down to room temperature, 20 ml water was carefully added and the precipitate was subsequently sucked off. 13.4 g (99%) 7-bromo-1H-pyrimido[5,4-b]indole-2,4(3H,5H)-dione was obtained. ESI-MS [m/z]: 278, 280 [M−H]−

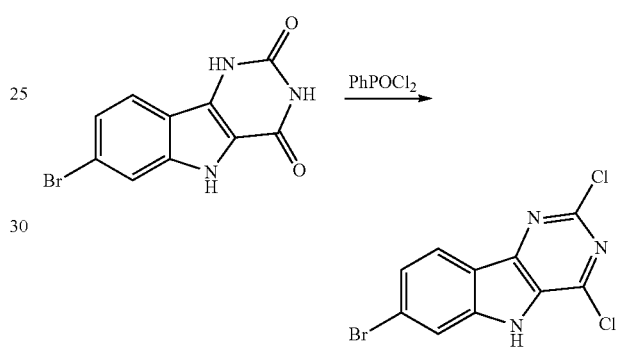

13.4 g (47 mmol) 7-bromo-1H-pyrimido[5,4-b]indole-2,4(3H,5H)-dione and 40 ml (287 mmol) dichlorophenylphosphinoxide was heated to 180° C. for 6 h. Having cooled down to room temperature, the mixture was poured onto 40 g ice water and neutralized with saturated sodium hydrogen carbonate solution. The resulting precipitate was sucked off and washed with water. 11.6 g (71%) 7-bromo-2,4-dichloro-5H-pyrimido[5,4-b]indole was obtained. ESI-MS [m/z]: 314, 316, 318 [M−H]−

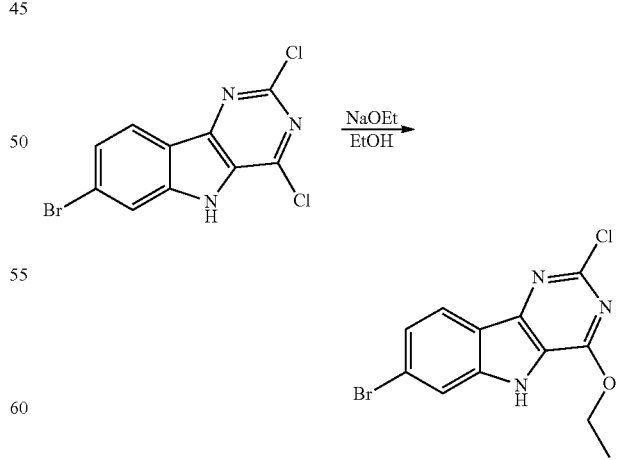

5 g (15.8 mmol) 7-bromo-2,4-dichloro-5H-pyrimido[5,4-b]indole was suspended in 20 ml ethanol and mixed with 15.8 ml (31.5 mmol) 2M sodium ethylate solution (EtOH). The mixture was refluxed for 9.5 h. Having cooled down to room temperature, the solvent was concentrated and water was added. The resulting precipitate was sucked off and washed with water. 5.1 g (99%) 7-bromo-2-chloro-4-ethoxy-5H-pyrimido[5,4-b]indole was obtained. ESI-MS [m/z]: 324, 326 [M−H]⁻ and sucked off. 1.3 g (87%) 7-bromo-2-chloro-4-(piperazin-1-yl)-5H-pyrimido[5,4-b]indole was obtained. ESI-MS [m/z]: 366, 368 [M+H]⁺

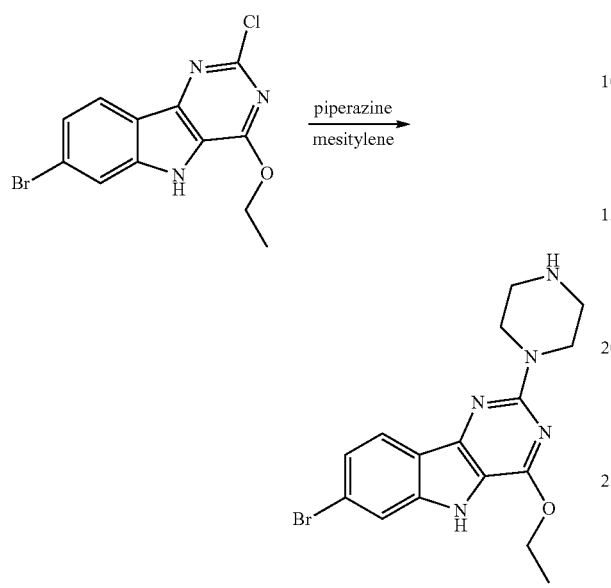

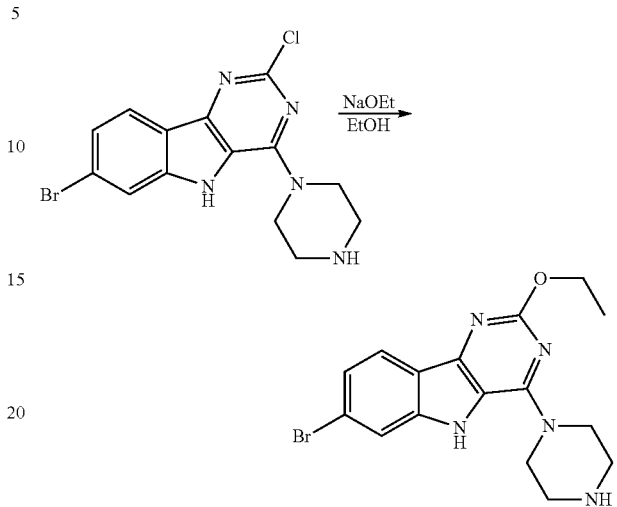

5.1 g (15.6 mmol) 7-bromo-2-chloro-4-ethoxy-5H-pyrimido[5,4-b]indole and 13.4 g (155.8 mmol) piperazine were heated in 80 ml mesitylene to 150° C. for 7.5 h. Then, the solvent was removed and the residue was suspended in water and sucked off. 5.8 g (99%) of the title substance was obtained. ESI-MS [m/z]: 376, 378 [M+H]⁺

200 mg (0.55 mmol) 7-bromo-2-chloro-4-(piperazin-1-yl)-5H-pyrimido[5,4-b]indole and 1.64 ml (1.64 mmol) 1 M NaOEt solution (EtOH) in 6 ml EtOH were heated in a microwave oven to 130° C. for 3 h. Then, the solvent was removed and the residue was suspended in water and sucked off. 200 mg (97%) of the title substance was obtained. ESI-MS [m/z]: 376, 378 [M+H]⁺

Example 5

Synthesis of 7-bromo-2-ethoxy-4-(piperazin-1-yl)-5H-pyrimido[5,4-b]indole

Example 6

Synthesis of 2-{7-bromo-2-(piperazin-1-yl)-5H-pyrimido-[5,4-b]indol-4-yloxy}ethanol

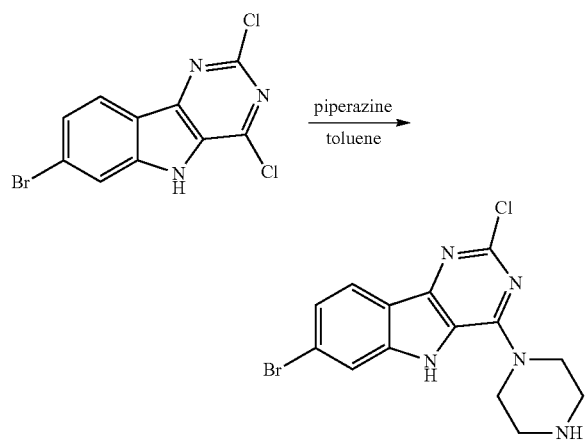

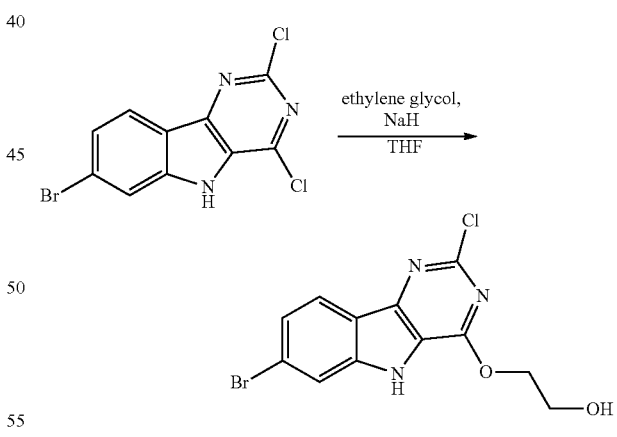

1.3 g (4.10 mmol) 7-bromo-2,4-dichloro-5H-pyrimido[5,4-b]indole (Example 4) and 1.3 g (14.8 mmol) piperazine were heated in 50 ml toluene at 65° C. for 3 h. Then, the solvent was removed and the residue was suspended in water 397 mg (6.4 mmol) ethylene glycol was added to 115 mg (4.8 mmol) NaH in 20 ml THF and the mixture was stirred at room temperature for 30 min. Then, 500 mg (1.6 mmol) 7-bromo-2,4-dichloro-5H-pyrimido[5,4-b]indole (Example 4) was added and the mixture was refluxed for 5 h. Thereafter, the solvent was removed and the residue was taken up in acetic ester and washed with saturated NaCl solution, dried over Na₂SO₄ and filtrated. Having removed the solvent, 450 mg (88%) 2-(7-bromo-2-chloro-5H-pyrimido[5,4-b]indol-4-yloxy)ethanol was obtained. ESI-MS [m/z]: 342, 344 [M+H]⁺

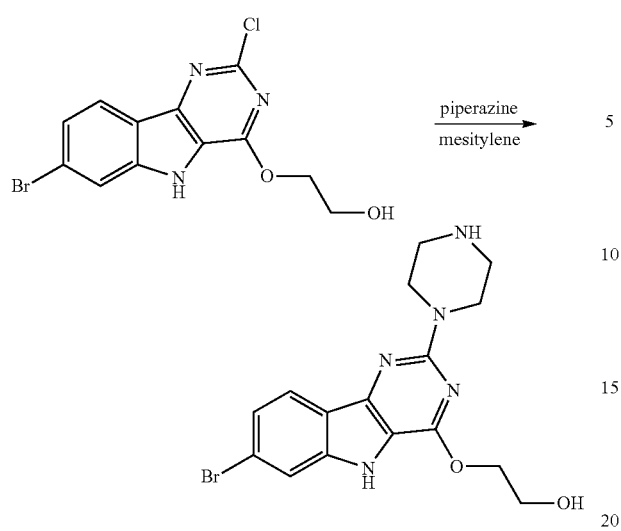

400 mg (1.17 mmol) 2-(7-bromo-2-chloro-5H-pyrimido[5,4-b]indol-4-yloxy)ethanol and 1.0 g (11.7 mmol) piperazine in 50 ml mesitylene were heated to 150° C. for 5 h. Then, the solvent was removed and the residue was taken up in EtOH and filtrated. Having removed the solvent, 250 mg (55%) of the title substance was obtained. ESI-MS [m/z]: 392, 394[M+H]$^+$ Example 7

Synthesis of 4-ethoxy-2-(piperazin-1-yl)-7-(pyridin-4-yl)-5H-pyrimido[5,4-b]indole

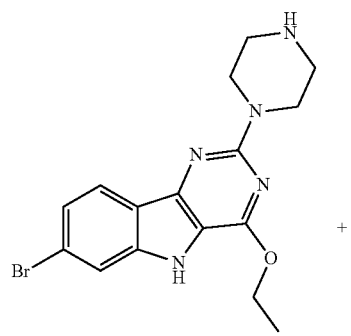

150 mg (0.4 mmol) 7-bromo-4-ethoxy-2-(piperazin-1-yl)-5H-pyrimido[5,4-b]indole (Example 4), 123 mg (0.6 mmol) 4-(4,4,5,5-tetramethyl-1,3,2-dioxaborolan-2-yl)pyridine, 276 mg (1.2 mmol) $K_3PO_4 \times H_2O$, 6.6 mg (16 mmol) S-Phos and 9.2 mg (8 mmol) $Pd(PPh_3)_4$ in 6 ml THF were heated in a microwave oven to 120° C. for 2 h. Then, the solvent was removed and following LC ($CH_2Cl_2$/MeOH, 0-20%) 93 mg (62%) of the title substance was obtained ESI-MS [m/z]: 375 [M+H]$^+$ The following compounds were obtained in analogy to Examples 4-7 (Table 3)

TABLE 3

| Structure | M [g/mol] | ESI MS [m/z] |
|---|---|---|
| 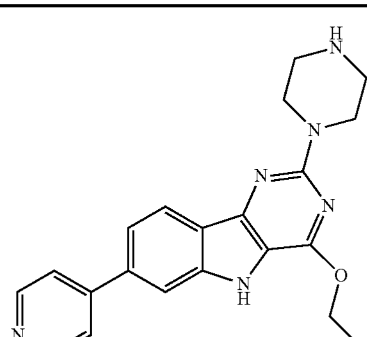 | 374.44 | 375 [M + H]$^+$ |

TABLE 3-continued

| Structure | M [g/mol] | ESI MS [m/z] |
|---|---|---|
| | 374.44 | 375 [M + H]+ |
| 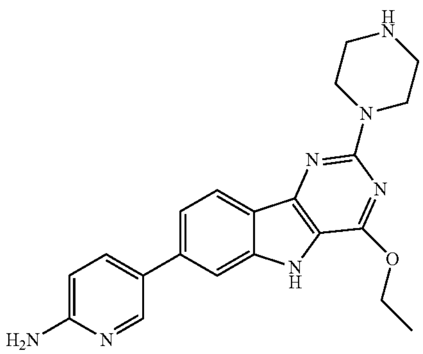 [SMILES: CCOc1nc(N2CCNCC2)nc2c1[nH]c1cc(-c3ccc(N)nc3)ccc12] | 389.45 | 390 [M + H]+ |
| 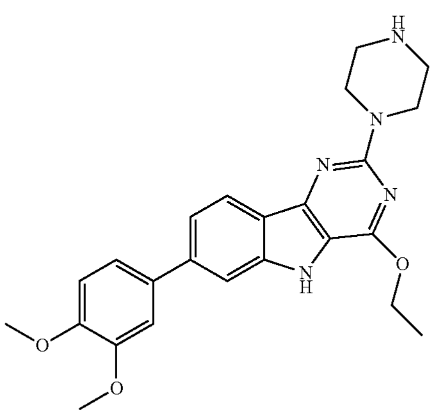 [SMILES: CCOc1nc(N2CCNCC2)nc2c1[nH]c1cc(-c3ccc(OC)c(OC)c3)ccc12] | 433.50 | 434 [M + H]+ |
| | 374.44 | 375 [M + H]+ |

TABLE 3-continued

| Structure | M [g/mol] | ESI MS [m/z] |
|---|---|---|
| 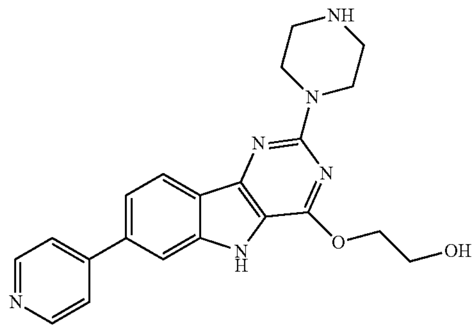 [SMILES: OCCOc1nc(N2CCNCC2)nc2c1[nH]c1cc(-c3ccncc3)ccc12] | 390.44 | 391 [M + H]+ |
| 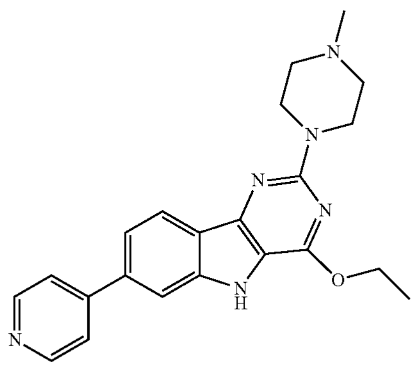 [SMILES: CCOc1nc(N2CCN(C)CC2)nc2c1[nH]c1cc(-c3ccncc3)ccc12] | 388.47 | 389 [M + H]+ |
| 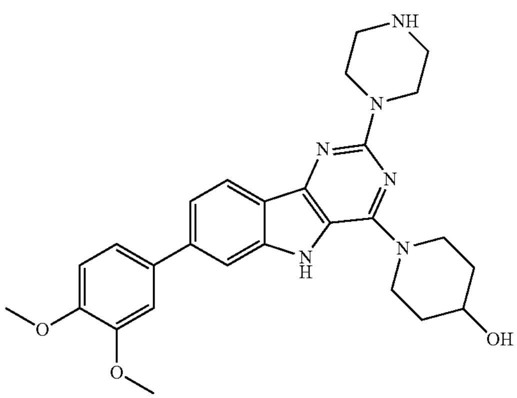 [SMILES: COc1ccc(-c2ccc3c(c2)[nH]c2c(N4CCC(O)CC4)nc(N4CCNCC4)nc23)cc1OC] | 488.58 | 489 [M + H]+ |
| 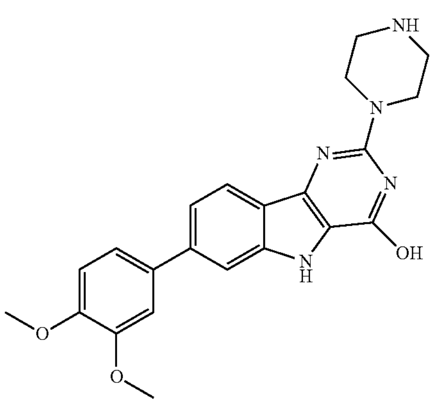 [SMILES: COc1ccc(-c2ccc3c(c2)[nH]c2c(O)nc(N4CCNCC4)nc23)cc1OC] | 405.45 | 406 [M + H]+ |

TABLE 3-continued
| Structure | M [g/mol] | ESI MS [m/z] |
|---|---|---|
| 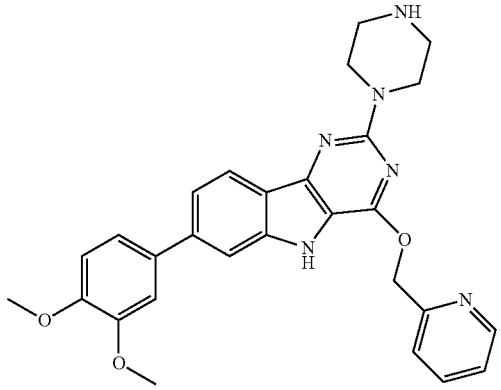 [SMILES: COc1ccc(-c2ccc3c(c2)[nH]c2c(OCc4ccccn4)nc(N4CCNCC4)nc23)cc1OC] | 496.56 | 497 [M + H]⁺ |
| 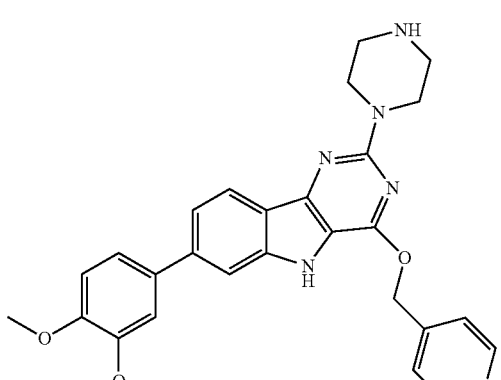 | 496.56 | 497 [M + H]⁺ |
| 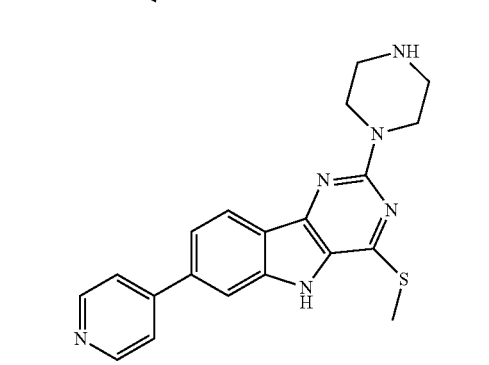 | 376.89 | 377 [M + H]⁺ |
| 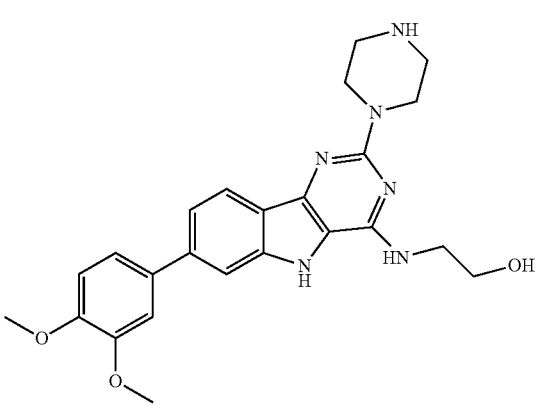 [SMILES: COc1ccc(-c2ccc3c(c2)[nH]c2c(NCCO)nc(N4CCNCC4)nc23)cc1OC] | 448.52 | 449 [M + H]⁺ |

TABLE 3-continued

| Structure | M [g/mol] | ESI MS [m/z] |
|---|---|---|
| 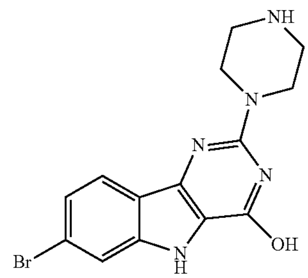 [SMILES: Oc1nc(N2CCNCC2)nc2c1[nH]c1cc(Br)ccc12] | 348.20 | 348.350 [M + H]+ |
| 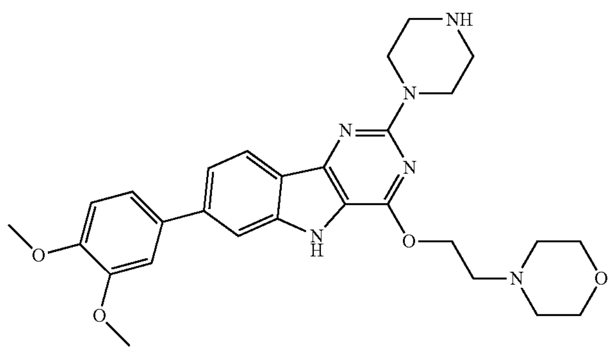 | 518.61 | 519 [M + H]+ |
| 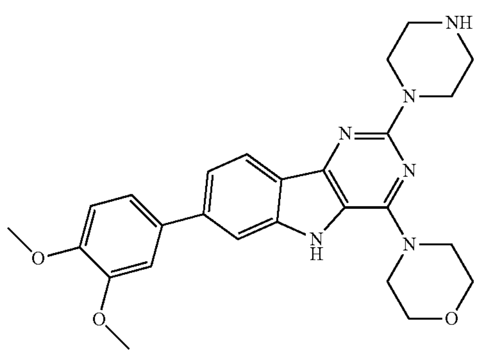 [SMILES: COc1ccc(-c2ccc3c(c2)[nH]c2c(N4CCOCC4)nc(N4CCNCC4)nc23)cc1OC] | 474.55 | 475 [M + H]+ |
| 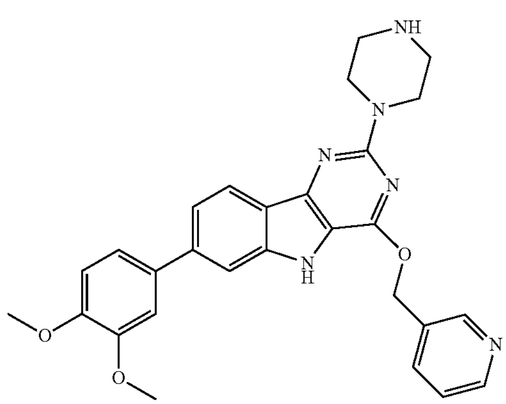 [SMILES: COc1ccc(-c2ccc3c(c2)[nH]c2c(OCc4cccnc4)nc(N4CCNCC4)nc23)cc1OC] | 496.56 | 497 [M + H]+ |

TABLE 3-continued

| Structure | M [g/mol] | ESI MS [m/z] |
|---|---|---|
| 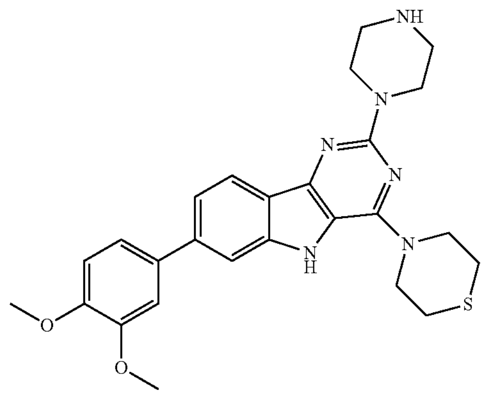 [SMILES: COc1ccc(-c2ccc3c(c2)[nH]c2c(N4CCSCC4)nc(N4CCNCC4)nc23)cc1OC] | 490.62 | 491 [M + H]+ |
| 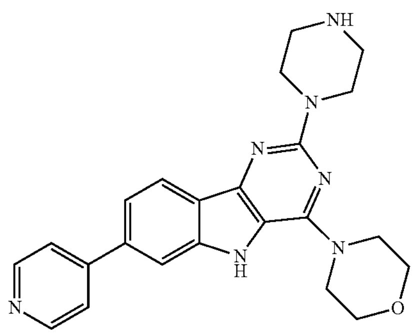 [SMILES: c1cc(-c2ccc3c(c2)[nH]c2c(N4CCOCC4)nc(N4CCNCC4)nc23)ccn1] | 415.49 | 416 [M + H]+ |
| 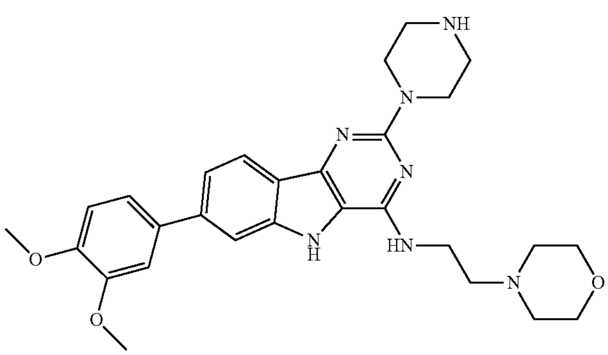 [SMILES: COc1ccc(-c2ccc3c(c2)[nH]c2c(NCCN4CCOCC4)nc(N4CCNCC4)nc23)cc1OC] | 517.62 | 518 [M + H]+ |
| 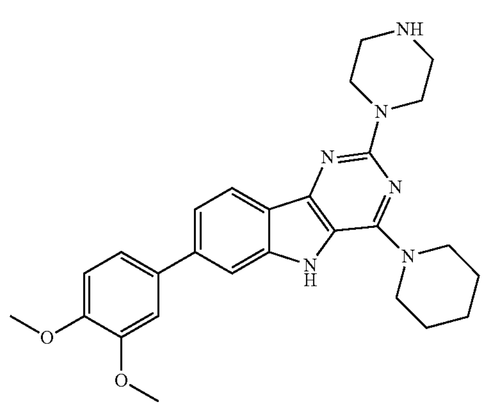 [SMILES: COc1ccc(-c2ccc3c(c2)[nH]c2c(N4CCCCC4)nc(N4CCNCC4)nc23)cc1OC] | 472.58 | 473 [M + H]+ |

TABLE 3-continued

| Structure | M [g/mol] | ESI MS [m/z] |
|---|---|---|
| 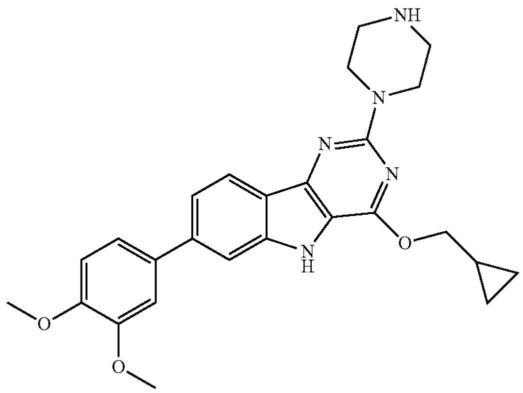 [SMILES: COc1ccc(-c2ccc3c(c2)[nH]c2c(OCC4CC4)nc(N4CCNCC4)nc23)cc1OC] | 459.54 | 460 [M + H]+ |
| 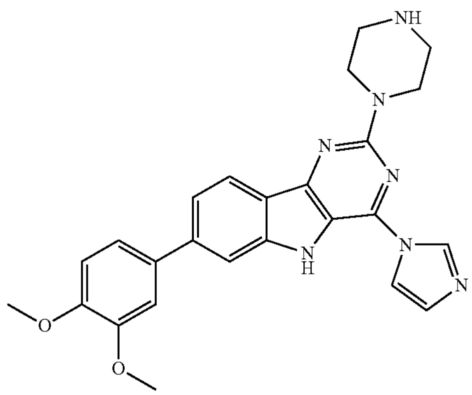 | 455.51 | 456 [M + H]+ |
| 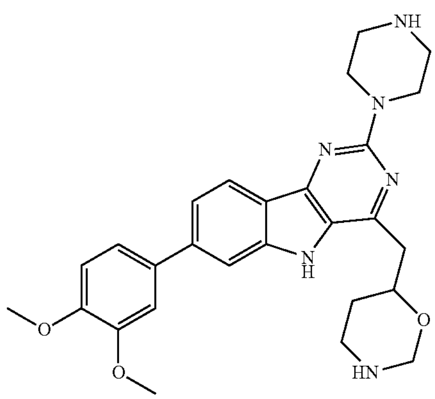 [SMILES: COc1ccc(-c2ccc3c(c2)[nH]c2c(CC4CCNCO4)nc(N4CCNCC4)nc23)cc1OC] | 488.58 | 489 [M + H]+ |
| 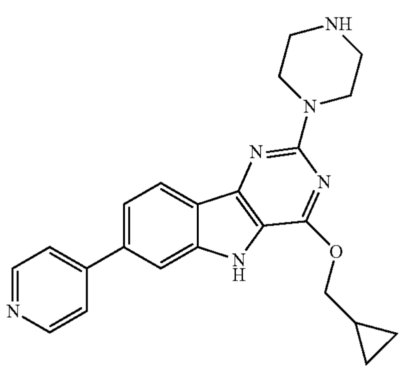 [SMILES: c1cc(-c2ccc3c(c2)[nH]c2c(OCC4CC4)nc(N4CCNCC4)nc23)ccn1] | 400.48 | 401 [M + H]+ |

TABLE 3-continued
| Structure | M [g/mol] | ESI MS [m/z] |
|---|---|---|
| 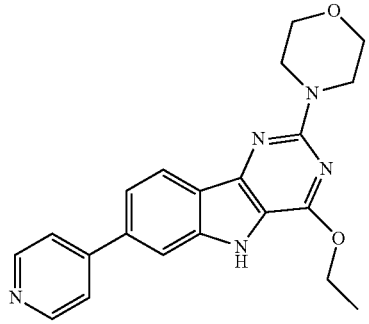 [SMILES: CCOc1nc(N2CCOCC2)nc2c1[nH]c1cc(-c3ccncc3)ccc12] | 375.42 | 376 [M + H]+ |
| 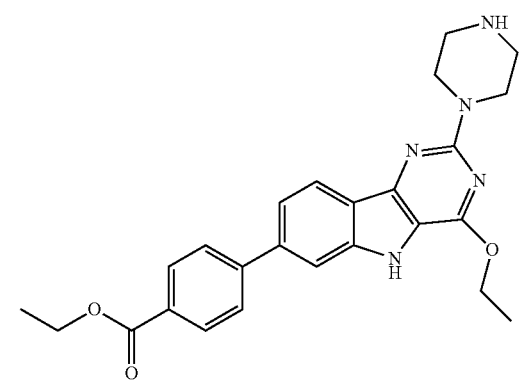 [SMILES: CCOC(=O)c1ccc(-c2ccc3c(c2)[nH]c2c(OCC)nc(N4CCNCC4)nc23)cc1] | 445.51 | 446 [M + H]+ |
| 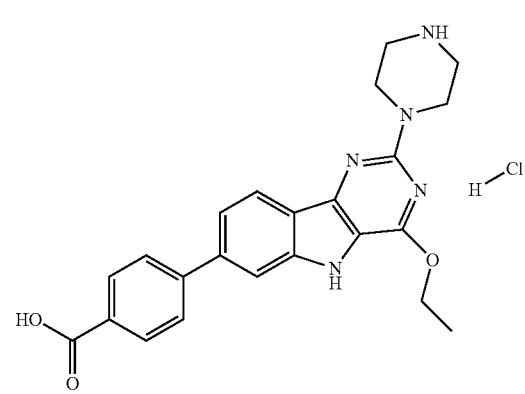 | 453.92 | 418 [M + H]+ |
| 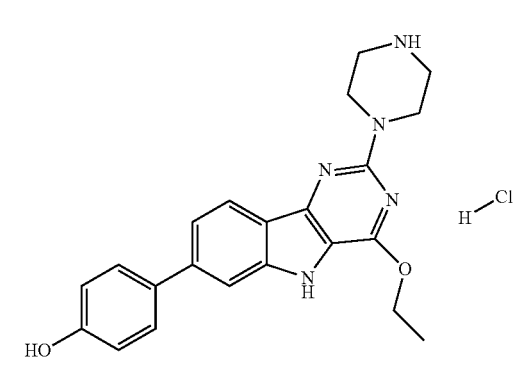 [SMILES: CCOc1nc(N2CCNCC2)nc2c1[nH]c1cc(-c3ccc(O)cc3)ccc12 ; Cl] | 425.91 | 390 [M + H]+ |

TABLE 3-continued

| Structure | M [g/mol] | ESI MS [m/z] |
|---|---|---|
| 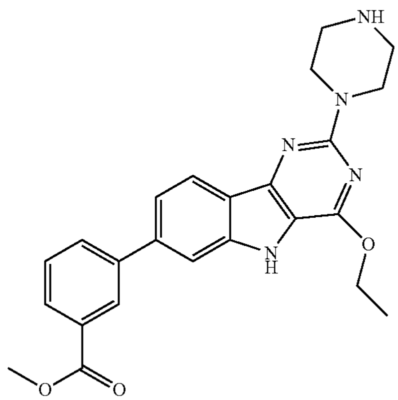 [SMILES: CCOc1nc(N2CCNCC2)nc2c1[nH]c1cc(-c3cccc(C(=O)OC)c3)ccc12] | 431.49 | 432 [M + H]⁺ |
| 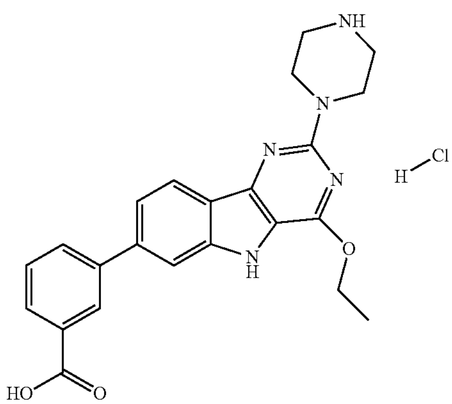 [SMILES: CCOc1nc(N2CCNCC2)nc2c1[nH]c1cc(-c3cccc(C(=O)O)c3)ccc12 ; Cl] | 453.92 | 418 [M + H]⁺ |
| 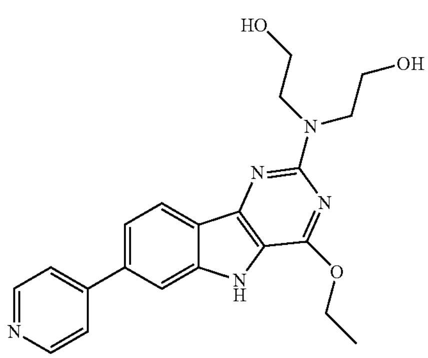 [SMILES: CCOc1nc(N(CCO)CCO)nc2c1[nH]c1cc(-c3ccncc3)ccc12] | 393.44 | 394 [M + H]⁺ |
| 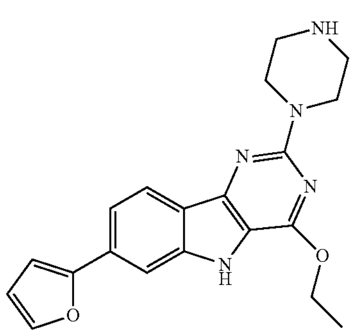 | 463.41 | 464 [M + H]⁺ |

TABLE 3-continued
| Structure | M [g/mol] | ESI MS [m/z] |
|---|---|---|
| 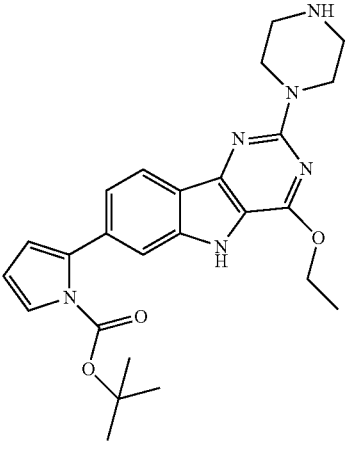 [SMILES: CCOc1nc(N2CCNCC2)nc2c1[nH]c1cc(-c3cccn3C(=O)OC(C)(C)C)ccc12] | 462.54 | 463 [M + H]⁺ |
| 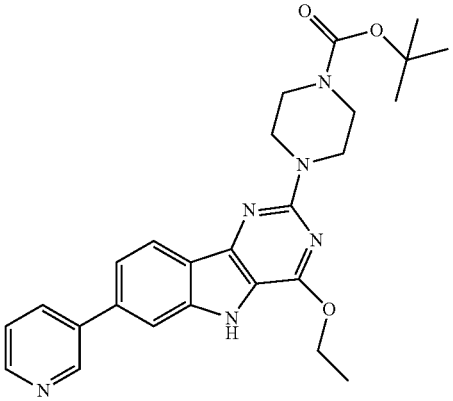 [SMILES: CCOc1nc(N2CCN(C(=O)OC(C)(C)C)CC2)nc2c1[nH]c1cc(-c3cccnc3)ccc12] | 474.55 | 475 [M + H]⁺ |
| 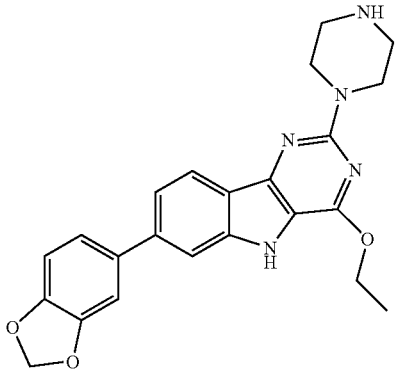 [SMILES: CCOc1nc(N2CCNCC2)nc2c1[nH]c1cc(-c3ccc4c(c3)OCO4)ccc12] | 417.46 | 418 [M + H]⁺ |

TABLE 3-continued

| Structure | M [g/mol] | ESI MS [m/z] |
|---|---|---|
| 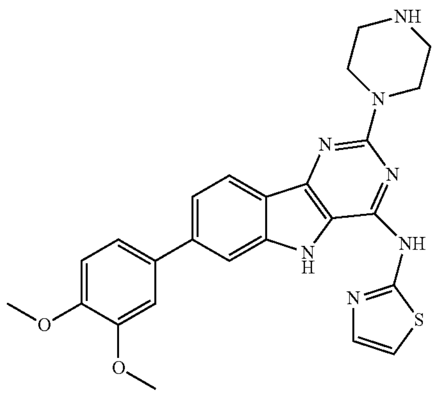 [SMILES: COc1ccc(-c2ccc3c(c2)[nH]c2c(Nc4nccs4)nc(N4CCNCC4)nc23)cc1OC] | 487.58 | 488 [M + H]+ |
| 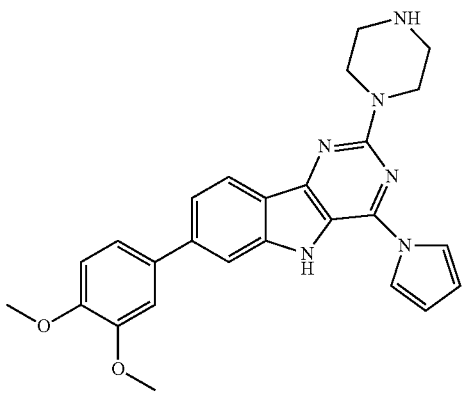 [SMILES: COc1ccc(-c2ccc3c(c2)[nH]c2c(-n4cccc4)nc(N4CCNCC4)nc23)cc1OC] | 454.52 | 455 [M + H]+ |
| 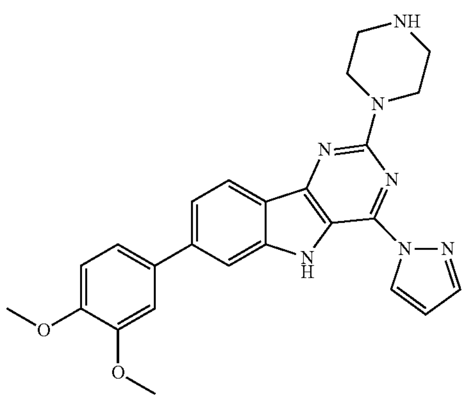 [SMILES: COc1ccc(-c2ccc3c(c2)[nH]c2c(-n4cccn4)nc(N4CCNCC4)nc23)cc1OC] | 455.51 | 456 [M + H]+ |
| 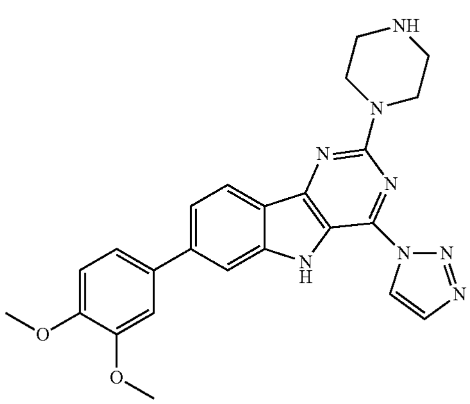 [SMILES: COc1ccc(-c2ccc3c(c2)[nH]c2c(-n4ccnn4)nc(N4CCNCC4)nc23)cc1OC] | 456.50 | 457 [M + H]+ |

TABLE 3-continued

| Structure | M [g/mol] | ESI MS [m/z] |
|---|---|---|
| 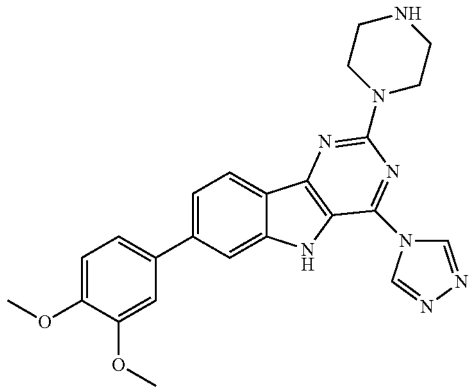 [SMILES: COc1ccc(-c2ccc3c(c2)[nH]c2c(-n4cnnc4)nc(N4CCNCC4)nc23)cc1OC] | 456.50 | 457 [M + H]+ |
| 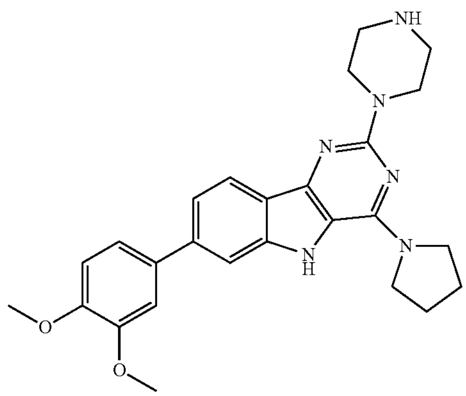 [SMILES: COc1ccc(-c2ccc3c(c2)[nH]c2c(N4CCCC4)nc(N4CCNCC4)nc23)cc1OC] | 458.56 | 459 [M + H]+ |

Example 8

Synthesis of 4-ethoxy-2-(piperazin-1-yl)-6-(pyridin-4-yl)-5H-pyrimido[5,4,-b]indole

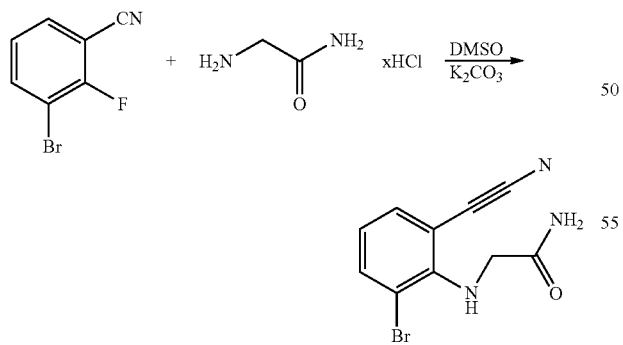

10.0 g (50.0 mmol) 3-bromo-2-fluorobenzonitrile, 11.1 g (100.0 mmol) glycinamide hydrochloride and 17.3 g (125 mmol) $K_2CO_3$ were suspended in 90 ml DMSO and heated at 100° C. for 4 h. Having cooled down to room temperature, the solvent was concentrated and water was added. The resulting precipitate was sucked off and washed with water. 10.8 g (85%) 2-(2-bromo-6-cyano-phenylamino)acetamide was obtained. ESI-MS [m/z]: 254, 256 [M+H]+

1.17 g (50.9 mmol) sodium was dissolved in 150 ml 2-propanol. Then, 10.82 g (42.6 mmol) 2-(2-bromo-6-cyano-phenylamino)acetamide was added and the solution was refluxed for 15 min. Thereafter, the reaction mixture was cooled to 0° C. and saturated $NH_4Cl$ solution was added. The solvent was concentrated, the resulting precipitate was sucked off and washed with water. 8.6 g (79%) 3-amino-7-bromo-1H-indole-2-carboxylic acid amide was obtained. ESI-MS [m/z]: 254, 256 [M+H]+

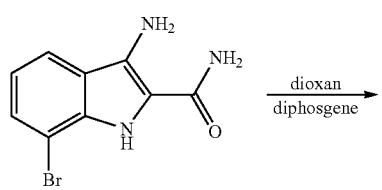

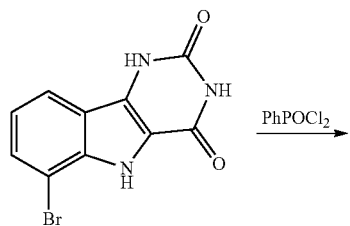

8.0 g (32 mmol) 3-amino-7-bromo-1H-indole-2-carboxylic acid amide was suspended in 50 ml dioxan, and refluxed after the addition of 3.8 ml (32 mmol) diphosgene for 3 h. Having cooled down to room temperature, 20 ml water was carefully added and the precipitate was then sucked off. 9.0 g (32%) 6-bromo-1H-pyrimido[5,4-b]indole-2,4(3H,5H)-dione was obtained. ESI-MS [m/z]: 278, 280 [M−H]⁻

9.0 g (32 mmol) 6-bromo-1H-pyrimido[5,4-b]indole-2,4 (3H,5H)-dione and 30 ml (215 mmol) dichlorophenylphosphinoxide were heated to 180° C. for 5 h. Having cooled down to room temperature, the mixture was poured onto 40 g ice water and neutralized with saturated sodium hydrogen carbonate solution. The resulting precipitate was sucked off and washed with water. 8.5 g (84%) 6-bromo-2,4-dichloro-5H-pyrimido[5,4-b]indole was obtained. ESI-MS [m/z]: 314, 316, 318 [M−H]⁻

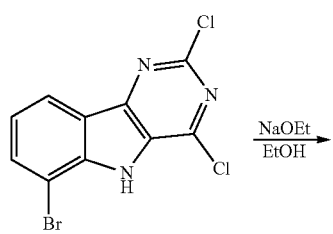

1.0 g (3.2 mmol) 6-bromo-2,4-dichloro-5H-pyrimido[5,4-b]indole was suspended in 5 ml absolute ethanol and mixed with 6 ml (6.4 mmol) 1M sodium ethylate solution (EtOH). The mixture was refluxed for 15 h. Having cooled down to room temperature, the solvent was concentrated and water was added. The resulting precipitate was sucked off and washed with water. 0.9 g (86%) 6-bromo-2-chloro-4-ethoxy-5H-pyrimido[5,4-b]indole was obtained. ESI-MS [m/z]: 324, 326 [M−H]⁻

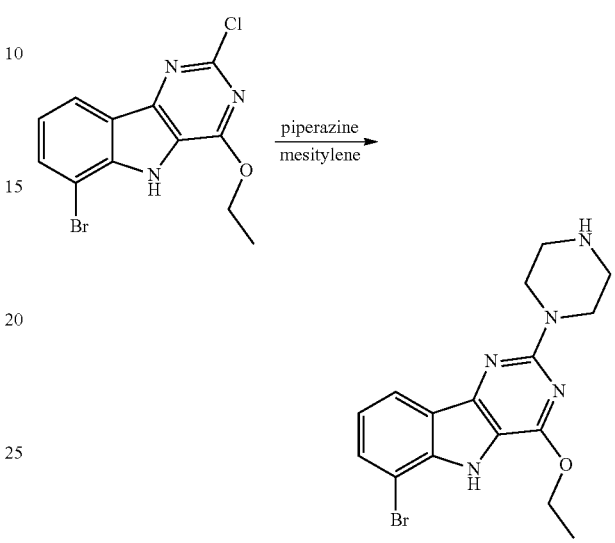

0.8 g (2.4 mmol) 6-bromo-2-chloro-4-ethoxy-5H-pyrimido[5,4-b]indole and 0.8 g (9.3 mmol) piperazine were refluxed in 10 ml mesitylene for 2.5 h. Then, the solvent was removed and the residue was suspended in water and sucked off. 0.8 g (85%) 6-bromo-4-ethoxy-2-(piperazin-1-yl)-5H-pyrimido[5,4-b]indole was obtained. ESI-MS [m/z]: 376, 378 [M+H]⁺

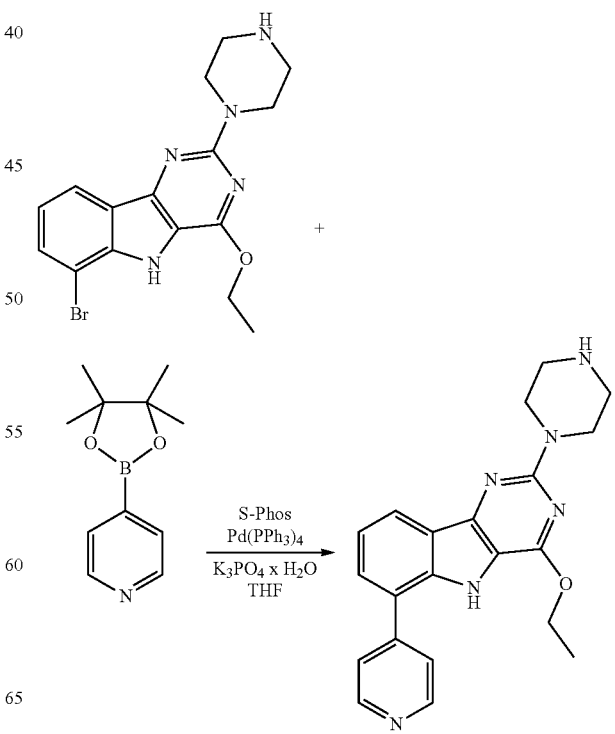

S-Phos = 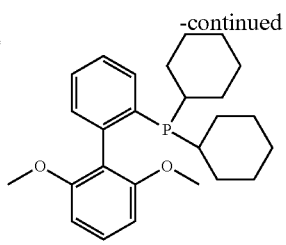

150 mg (0.4 mmol) 6-bromo-4-ethoxy-2-(piperazin-1-yl)-5H-pyrimido[5,4-b]indole (Example 4), 183 mg (0.9 mmol) 4-(4,4,5,5-tetramethyl-1,3,2-dioxaborolan-2-yl)pyridine, 276 mg (1.2 mmol) $K_3PO_4 \times H_2O$, 6.6 mg (16 μmol) S-Phos and 9.2 mg (8 μmol) $Pd(PPh_3)_4$ in 6 ml THF were heated in a microwave oven to 120° C. for 5 h. Then, the solvent was removed and following LC ($CH_2Cl_2$/MeOH, 0-20%) 112 mg (75%) of the title substance was obtained. ESI-MS [m/z]: 375 $[M+H]^+$ Example 9

Synthesis of 4-ethoxy-7-morpholino-2-(piperazin-1-yl)-5H-pyrimido[5,4-b]indole

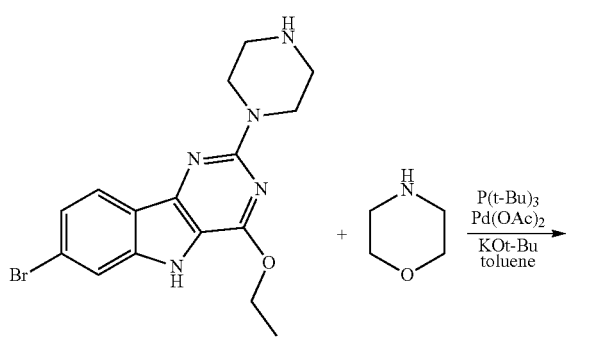

100 mg (0.27 mmol) 7-bromo-4-ethoxy-2-(piperazin-1-yl)-5H-pyrimido[5,4-b]indole (Example 4), 164 μl (1.86 mmol) morpholine, 179 mg (1.59 mmol) KOt-Bu, 1.2 mg (5.4 μmol) $Pd(OAc)_2$ and 4.4 mg (21.6 μmol) $P(t-Bu)_3$ were heated in 6 ml toluene in a microwave oven to 140° C. for 3 h. Then, the solvent was removed and the residue was purified by preparative HPLC (RP18). 8 mg (8%) of the title substance was obtained. ESI-MS [m/z]: 383 $[M+H]^+$ The following compounds were obtained in analogy to Example 9 (Table 4)

TABLE 4

| Structure | M [g/mol] | ESI MS [m/z] |
|---|---|---|
| 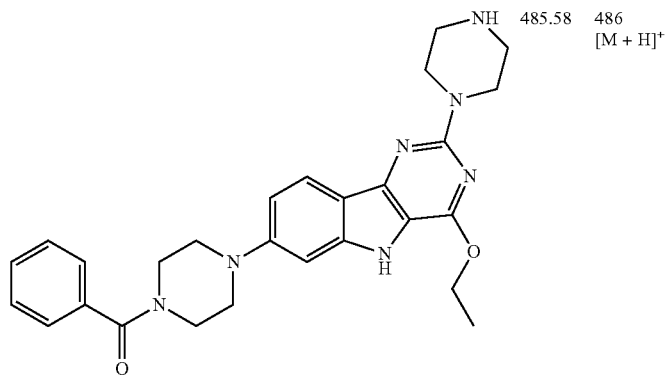 | 485.58 | 486 $[M + H]^+$ |

TABLE 4-continued

| Structure | M [g/mol] | ESI MS [m/z] |
|---|---|---|
| 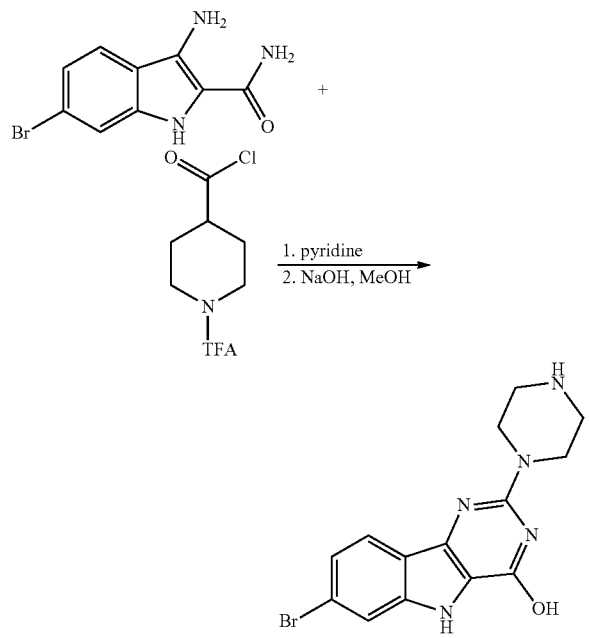 | 459.55 | 460 [M + H]+ |

Example 10

Synthesis of 7-bromo-4-ethoxy-2-(4-piperidyl)-5H-pyrimido[5,4-b]indole 767 mg (3.15 mmol) 1-(2,2,2-trifluoroacetyl)piperidine-4-carboxylic acid chloride dissolved in $CH_2Cl_2$ was slowly added drop-wise to 526 mg (2.10 mmol) 3-amino-6-bromo-1H-indole-2-carboxylic acid amide (Example 4) in pyridine at 0° C. Then, stirring was carried out at room temperature for 40 min. After the addition of water, the solvent was removed in vacuo and the residue was taken up in methanol. After the addition of 2 M NaOH (excess), the reaction was kept at reflux for 45 min. Thereafter, the methanol was removed in vacuo, the precipitate was sucked off and washed with water. 652 mg (89%) 7-bromo-2-(4-piperidyl)-5H-pyrimido[5,4-b]indol-4-ol was obtained. ESI-MS [m/z]: 347, 349 [M+H]+

650 mg (1.90 mmol) 7-bromo-2-(4-piperidyl)-5H-pyrimido[5,4-b]indol-4-ol were kept at reflux in $POCl_3$ for 9 h. Then, $POCl_3$ was removed in vacuo, the residue was mixed with water and neutralized with $NaHCO_3$. The precipitate formed was sucked off and washed with water. 500 mg (72%) 7-bromo-4-chloro-2-(4-piperidyl)-5H-pyrimido[5,4-b]indole was obtained. ESI-MS [m/z]: 365, 367 [M+H]+

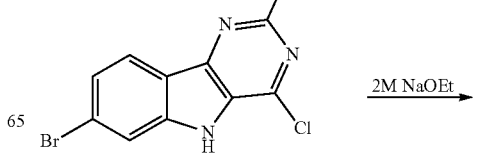

-continued

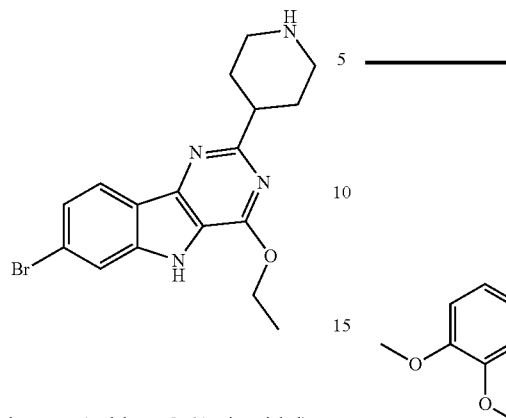

300 mg (0.82 mmol) 7-bromo-4-chloro-2-(4-piperidyl)-5H-pyrimido[5,4-b]indole was mixed with an excess of 2 M NaOEt and kept at reflux for 2 h. Then, water was added and the solvent was removed in vacuo. Following LC (CH$_2$Cl$_2$/MeOH, 0-50%), 160 mg (52%) of the title substance was obtained ESI-MS [m/z]: 375, 377 [M+H]$^+$ The following compounds were obtained in analogy to Examples 7 and 10 (Table 5)

TABLE 5

| Structure | M [g/mol] | ESI MS [m/z] |
|---|---|---|
|  | 373.45 | 374 [M + H]$^+$ |
|  | 432.51 | 433 [M + H]$^+$ |

TABLE 5-continued

| Structure | M [g/mol] | ESI MS [m/z] |
|---|---|---|
|  | 432.51 | 433 [M + H]$^+$ |
| 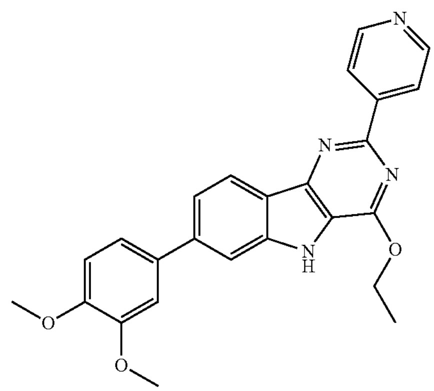 [SMILES: CCOc1nc(-c2ccncc2)nc2c1[nH]c1cc(-c3ccc(OC)c(OC)c3)ccc12] | 426.47 | 427 [M + H]$^+$ |
| 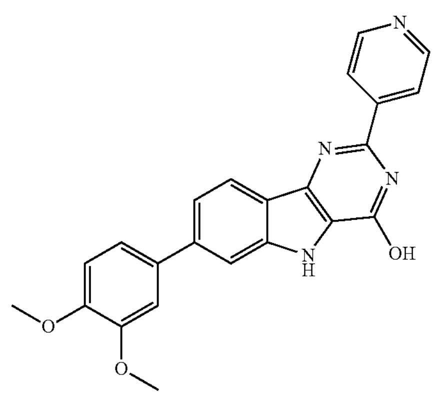 [SMILES: COc1ccc(-c2ccc3c(c2)[nH]c2c(O)nc(-c4ccncc4)nc23)cc1OC] | 398.41 | 399 [M + H]$^+$ |

Example 11

Induction of Apoptosis in Chronic Lymphatic Leukemia (B-CLL)

Compounds according to the invention were tested as inductors of a cytotoxic reaction, i.e. triggering of apoptosis, in the case of chronic lymphatic leukemia (B-CLL).

Fludarabine, which is used in B-CLL as a standard chemotherapeutic agent, was employed as a positive control. A cytotoxicity up to a maximum of 60% was achievable under equal test conditions.

The cytotoxicity of the B-CLL cells was determined by means of a commercially available formazane reduction assay (MMT test) after 24 h of incubation of the patient's blood with the active substances.

The following list shows a selection of the substances according to the invention which trigger ex vivo in the blood of B-CLL patients a cytotoxicity (apoptosis) in up to 100% of the leukemia cells and were investigated in the below experiments with respect to their abilities:

2-(4-ethoxy-9-methoxy-2-(piperazin-1-yl)-5H-pyrimido[5,4-b]indol-7-yl)benzeneamine 2-{2-(piperazin-1-yl)-7-(pyridin-4-yl)-5H-pyrimido[5,4-b]indol-4-yloxy}ethanol 2-ethoxy-4-(piperazin-1-yl)-7-(pyridin-4-yl)-5H-pyrimido[5,4-b]indole 4-ethoxy-2-(4-methylpiperazin-1-yl)-7-(pyridin-4-yl)-5H-pyrimido[5,4-b]indole 4-ethoxy-2-(piperazin-1-yl)-6-(pyridin-4-yl)-5H-pyrimido[5,4-b]indole 4-ethoxy-2-(piperazin-1-yl)-7-(2-aminopyridin-5-yl)-5H-pyrimido[5,4-b]indole 4-ethoxy-2-(piperazin-1-yl)-7-(3,4-dimethoxy-phenyl)-5H-pyrimido[5,4-b]indole 4-ethoxy-2-(piperazin-1-yl)-7-(pyridin-3-yl)-5H-pyrimido[5,4-b]indole 4-ethoxy-2-(piperazin-1-yl)-7-(pyridin-4-yl)-5H-pyrimido[5,4-b]indole 4-ethoxy-2-(piperazin-1-yl)-8-(pyridin-4-yl)-5H-pyrimido[5,4-b]indole 4-ethoxy-7-morpholino-2-(piperazin-1-yl)-5H-pyrimido[5,4-b]indole 4-ethoxy-9-methoxy-2-(piperazin-1-yl)-7-(pyridin-4-yl)-5H-pyrimido[5,4-b]indole 4-(4-ethoxy-2-(piperazin-1-yl)-5H-pyrimido[5,4-b]indol-7-yl)benzoic acid ethyl ester 4-(4-ethoxy-2-(piperazin-1-yl)-5H-pyrimido[5,4-b]indol-7-yl)benzoic acid hydrochloride 4-(4-ethoxy-2-(piperazin-1-yl)-5H-pyrimido[5,4-b]indol-7-yl)phenol-hydrochloride 3-(4-ethoxy-2-(piperazin-1-yl)-5H-pyrimido[5,4-b]indol-7-yl)benzoic acid methyl ester 3-(4-ethoxy-2-(piperazin-1-yl)-5H-pyrimido[5,4-b]indol-7-yl)benzoic acid hydrochloride Detection of Apoptosis Inducing Effect of the Substances According to the Invention on Human Blood Cells In order to check the selective effect of various substances as to the vitality of human cells, isolated B cells from patients suffering from chronic B cell leukemia (B-CLL) and also purified white blood platelets (PBMC) and erythrocytes from healthy donors were investigated. The permanent human EHEB B-CLL cell line was selected as a model system for the chronic lymphatic B cell leukemia. It is known in the literature that as compared to primary B-CLL cells the EHEB cells respond in a much more insensitive fashion to proapoptotic signals. The cells were incubated with concentration series of the test substances for 3 days and the vitality of the cells was determined by means of CellTiter-Glo™ ATP assay (Promega, catalog number G7571) according to the manufacturer's instructions after this period.

Isolation and Purification of Primary Human B-CLL Cells and Healthy Human PBMCs

Primary tumor cells are isolated from whole blood by means of density gradient centrifugation. To this end, the patient's whole blood is incubated with 50.0 µl human B cell enrichment cocktail (RosetteSep; Stem Cell Technology, Cat #15064) per milliliter whole blood at room temperature (RT) for 20 min. Then, the whole blood is diluted at a ratio of 1:1 with phosphate buffered saline solution (PBS; PAA, catalog no. H15-002) with 2% fetal calf serum (FCS; PAA, catalog no. A15-151). Having added the required volume of a ficoll paque plus solution (GE Healthcare, catalog no. 17-1440-02; see manufacturer's instructions) to a centrifugation tube (TPP, catalog no. 91015, or 91016, or 91050), this solution is carefully overlaid by means of a corresponding volume of dilute whole blood (see manufacturer's instructions) and centrifuged at 2500 rpm at RT for 20 minutes. After this centrifugation, the cell rich interphase/intermediate layer is carefully removed and transferred to a new centrifugation tube. In order to wash the cells, an equal volume PBS/2% FCS is added and the suspension is centrifuged at 1200 rpm and RT for 5 minutes. After careful removal of the wash solution, the cell pellet is resuspended in 10 ml complete cell culture medium (RPMI 1640, PAA catalog no. E15-840, with 10% FCS, 1% penicillin/streptomycin, PAA, catalog no. P11-010). Having determined the cell number by means of trypan blue staining (trypan blue solution of Sigma-Aldrich, catalog no. T-8154) the desired number of test plates can be prepared.

Preparation of Isolated, Primary, Human B-CLL Cells for the Test

After determining the cell number, the required volume of a cell suspension having $2.86 \times 10^6$ cells per milliliter is produced in each case in complete cell culture medium. The cells are seeded in a density of $2.86 \times 10^5$ cells per cavity in 70 µl complete cell culture medium in a 96-well measurement plate (Costar, catalog no. 3610) and cultured at 37° C., 5% $CO_2$, overnight. The test substance(s) are added the next day. Having added the test substance(s), the cells are available at a density of $2.00 \times 10^5$ in 100 µl complete cell culture medium.

Treatment of the Cells with Test Substance(s)

In accordance with their solubility, the test substances are dissolved in dimethyl sulfoxide (DMSO, Sigma-Aldrich, catalog no. 276855) at a molar concentration from $1.00 \times 10^{-3}$ to $1.00 \times 10^{-1}$. Dilution series are produced in the solvent DMSO from these stock solutions; the number of dilutions depends on the number of test substances to be measured and the number of test plates. If possible, eight dilutions are prepared which cover a molar concentration range of about $1.00 \times 10^{-3}$ to $1.00 \times 10^{-9}$. The test substance(s) are added to 30 µl complete cell culture medium, the end concentration of the solvent DMSO being at most 1%. Cells which are only treated with the solvent DMSO at a final concentration of 1% serve as a control. Having added the test substance dilution(s), the cells are available at a density of $2.0 \times 10^5$ in 100 µl complete cell culture medium per well. The thus treated cells are now incubated at 37° C., 5% $CO_2$, for 72 h.

Determination of Cytotoxicity

The toxic effect of the test substance(s) is determined by means of the CellTiter-Glo™ ATP assay (Promega, catalog number G7571) according to the manufacturer's instructions. This method detects the still vital cells by means of the available ATP which the living cells need to maintain the metabolism. This ATP converts an added luminescence substrate thus generating a light signal. The luminescence is recorded by means of the FLUOstar Optima Reader (BMG Labtechnologies) and converted into numerical values. A dose effect curve is then drawn by means of the sigma plot evaluation software (SYSTAT, version 6 for Windows) and the effective concentration which kills 50% of the cells ($EC_{50}$ concentration) is determined.

Vitality Test

In order to detect the cell activity, the fluorescence indicator resazurine was added by pipetting in a proportion of 10% (v/v) after the incubation period and the cells were incubated in an incubator for another 4 h. In this connection, the non-fluorescent resazurine is converted by vital cells in the mitochondria thereof into a fluorescent dye whose intensity is proportional to the number of the vital cells. The fluorescence intensity was measured after the incubation period at an excitation wavelength of 530 nm and an emission wavelength of 590 nm with a FluostarOPTIMA (BMG Labtechnologies) microplate reader.

Evaluation of the Results

By means of the relative fluorescence values, the percents of dead cells were calculated as compared to the solvent control (DMSO) and these values were plotted against the substance concentration. Dose-effect curves were prepared with the Sigma Pilot program and the $EC_{50}/IC_{50}$ values were calculated for each substance by means of these trajectories. The $IC_{50}$ values for the substances according to the invention are between 0.1 and 5 µM.

Influence of the Substances According to the Invention on B-CLL Cells

The apoptosis inducing effect of the substances listed in Example 11 on purified B lymphocytes from patients suffering from chronic B-CLL depicted a strong interindividual variation width which showed that the patients were divided into groups showing strong, medium and weak responses to the active substances according to the invention. Table 6 depicts the results of the apoptosis inducing effect of the substances.

TABLE 6

Influence of the substances according to the invention on the vitality of B-CLL cells

| Responder | Number of patients | Cytotoxicity ($EC_{50}$ µM) |
| --- | --- | --- |
| total | n = 30 | 1.83 ± 0.95 |
| strong | n = 9 | 0.679 ± 0.45 |
| medium | n = 19 | 2.081 ± 1.32 |
| weak | n = 2 | 7.24 ± 3.61 | strong ($EC_{50}$ 10 nM-1 µM)
medium ($EC_{50}$ 1.1 µM-5 µM)
weak ($EC_{50}$ >5 µM)

Table 6 depicts the average values of the compounds mentioned in Example 11.

As shown in Table 6, the substances according to the invention have a cytotoxic effect on the leukemic B-CLL cells. It was striking that in the investigated patient's blood, a different responsibility to the substances according to the invention was observed.

Influence of the Substances According to the Invention on the Vitality of Leukemic B Cells in B-CLL Patients with an 11q Deletion As shown in FIG. 1 by way of example, the leukemic B lymphocytes from B-CLL patients with an 11q deletion respond in a particularly sensitive way to the apoptosis inducing effect of the substances according to the invention. The FIG. 1 illustration shows by means of example the effect of the substance according to the invention, i.e. 4-ethoxy-2-(piperazin-1-yl)-7-(pyridin-4-yl)-5H-pyrimido[5,4-b]indole, on such a patient.

As shown, the $IC_{50}$ which is 80 nM is markedly better than the average value of all B-CLL patients ($IC_{50}$ 1.83±0.95 µM), which proves that patients with this chromosomal deletion respond in a much more sensitive way to the treatment with the substances according to the invention.

Furthermore, it was of interest whether the substances according to the invention can trigger apoptosis in healthy blood cells as well.

TABLE 7

Influence of the substances according to the invention on the vitality of healthy PBMCs

| PBMC cells ($EC_{50}$ µM) | B-CLL cells ($EC_{50}$ µM) |
| --- | --- |
| 29.49 ± 13.4 µM<br>n = 23 | 1.83 ± 0.95<br>n = 30 |

As shown in Table 7, B-CLL cells having an $EC_{50}$ of 1.83±0.95 µM are e.g. influenced by the substances according to the invention about 16 times more strongly than healthy PBMC cells having an $EC_{50}$ of 29.49±13.4 µm. Thus, it was possible to show free of doubt that the substances according to the invention have a very good therapeutic effect on leukemia cells without attacking the other healthy blood cells. The direct action comparison between fludarabine as a current golden standard with the substances according to the invention in the blood of B-CLL patients also shows an $EC_{50}$ value from 2 µM to 200 µM for fludarabine (literature and own values) while the substances according to the invention have $EC_{50}$ values from 10 nM to 5 µM.

Detection of Apoptosis

In order to determine the specific induction of programmed cell death (apoptosis), a detection thereof was carried out by means of caspase-3/7 activity; the caspase-3/7 activity is described in the literature as a safe detection of apoptosis.

The EHEB cells were prepared as described above and incubated with three concentration dilutions, each in triple determination, for 4.5 and 24 hours. Thus, substance final concentrations were selected from 50.0, 10.0 and 2.00 µM for the 4 hour batches as well as 10.0, 1.00 and 0.50 µM for the 24 hour batches. In this connection, staurosporine in a final concentration of 2.00 µM (4 hour batches) and 0.50 µM (24 hour batches) acted as the positive control. In order to detect the caspase-3/7 activity, the caspase-Glo 3/7 and caspase-Glo 9 assays of Promega company were used; in this connection, the enzyme activity was determined by means of a luminescence signal which was recorded with the FluostarOPTIMA measurement device (BMG Labtechnologies).

The results were evaluated by a comparison between the relative luminescence intensity of the test substances and the positive control (staurosporine=100%) by means of the Excel program. The relative intensities for the substances according to the invention are up to 100% with an inhibitor concentration between 1 and 50 µM.

In this test batch, DMSO served as a negative control at the same final concentration of 1% at which the active substances were also dissolved.

Figure 2:
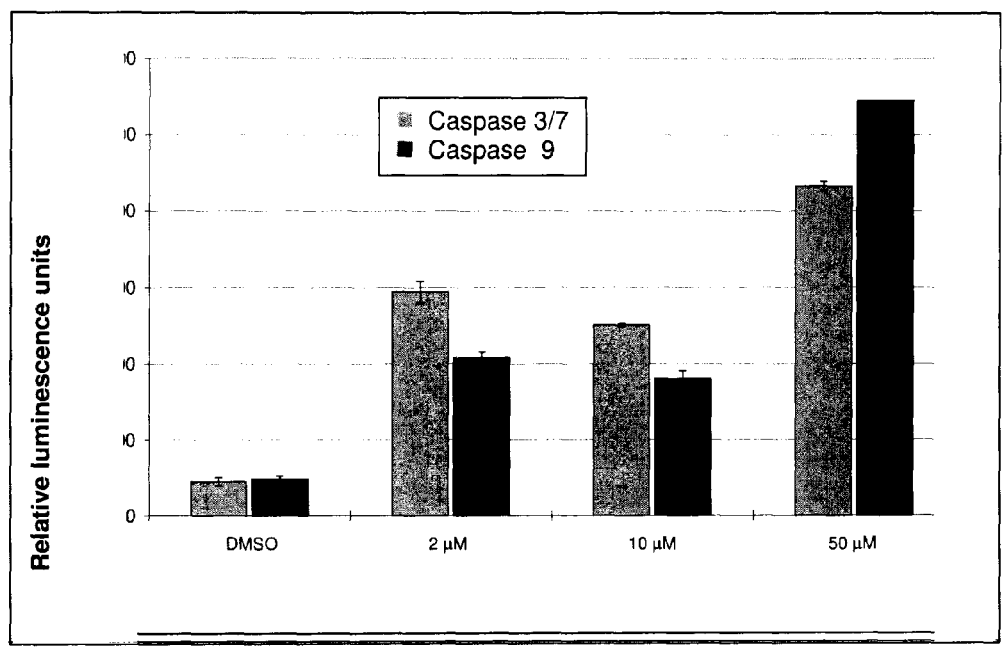
FIG. 2 is a graph showing the effect of the substance according to the invention, i.e. 4-ethoxy-2-(piperazin-1-yl)-7-(pyridin-4-yl)-5H-pyrimido[5,4-b]indole, in activating caspases 3, 7, and 9.

The FIG. 2 illustration exemplifies the effect of the substance according to the invention, i.e. 4-ethoxy-2-(piperazin-1-yl)-7-(pyridin-4-yl)-5H-pyrimido[5,4-b]indole, in activating caspases 3, 7, and 9.

As shown, the trigger enzymes decisive for apoptosis, i.e. caspases 3, 7 and 9, are activated in the permanent B-CLL cell line EHEB after incubation with the substances according to the invention depending on the concentration. These findings can also be confirmed in the leukemic B-CLL cells (results are not shown here). This data clearly proves that the cell cytotoxicity caused by the substances according to the invention is no toxic effect which results in the necrosis of the cells but an induction of apoptosis.

Example 12

Hemolysis Assay

From the remaining erythrocyte residue after the collection of PBMC, a corresponding volume of erythrocytes was taken and used for the test. For this purpose, the erythrocytes were diluted 1:100 (v/v) in RPMI 1640 medium (phenol red free) with 2% Ultroser HY. 100 µl of this suspension was added by pipetting into each well of a 96 well round bottom plate. Then, 100 µl of a twofold concentrated test substance dilution series and in each case a twofold concentrated saponine dilution series were added to the erythrocytes. The determination was made in triple batches. Saponine served as a positive control. The batches were incubated in the dark at room temperature on a shaker for 2 h. Thereafter, the plate was centrifuged at 300 RPM for 10 min. and 100 µl of the supernatants each was transferred into a new 96-well flat bottom plate. The lysis was determined by the measurement of the haemoglobin absorption at 414 nm against a reference wavelength of 620 nm.

Figure 3:
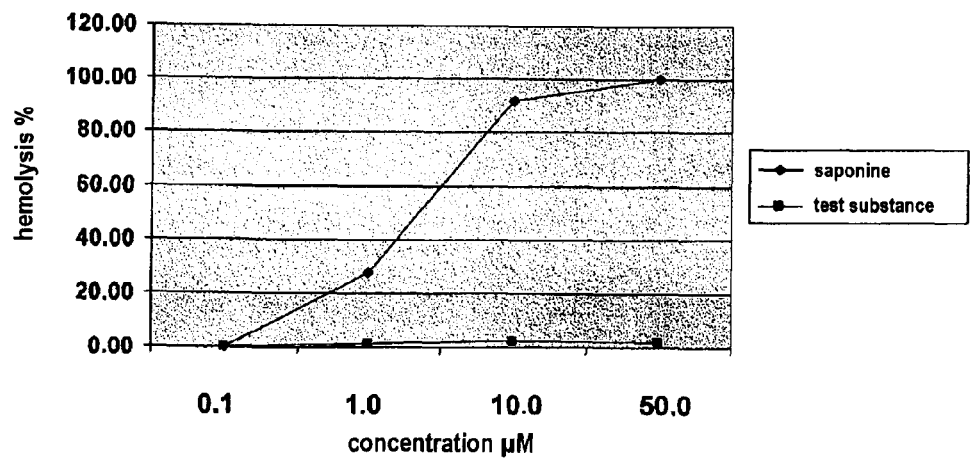
FIG. 3 is a graph of the hemolysis effect of the substance according to the invention, i.e. 4-ethoxy-2-(piperazin-1-yl)-7-(pyridin-4-yl)-5H-pyrimido[5,4-b]indole.

The FIG. 3 illustration exemplifies the effect of the substance according to the invention, i.e. 4-ethoxy-2-(piperazin-1-yl)-7-(pyridin-4-yl)-5H-pyrimido[5,4-b]indole.

The substances according to the invention do not hemolyse the human erythrocytes in contrast to the positive control, i.e. saponine.

Example 13

Synergistic Effect of the Substances According to the Invention with Fludarabine If purified B-CLL cells containing the substances according to the invention are incubated together with the nucleoside analogon, i.e. fludarabine, there is a synergistic effect of both substances on the induction of apoptosis.

Figure 4:
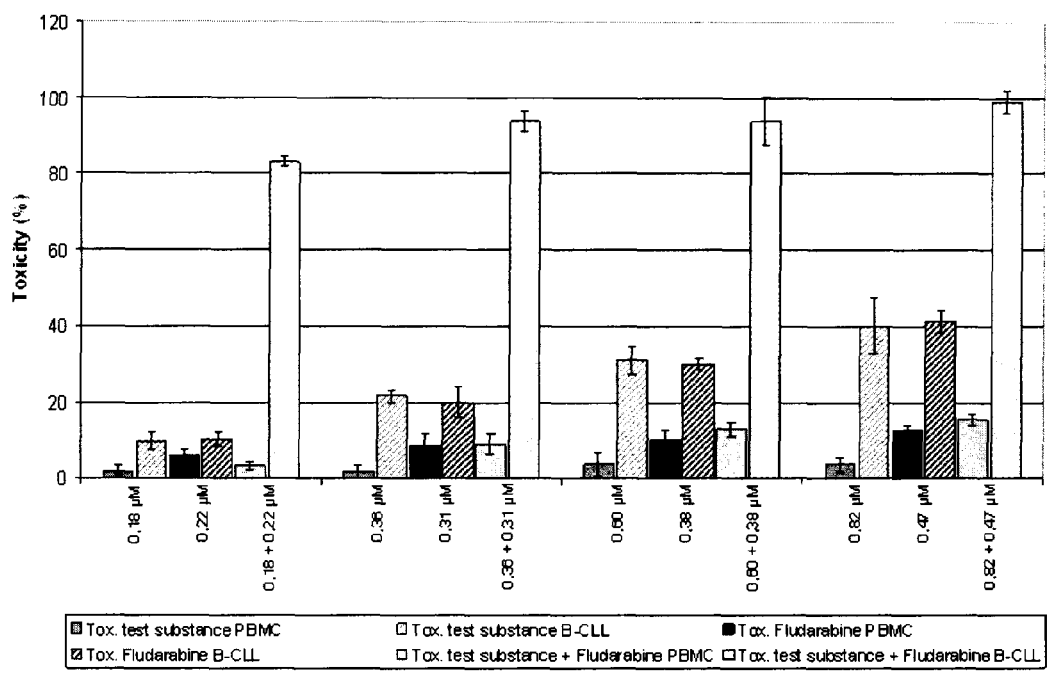
FIG. 4 is a graph showing the synergistic effect of the substance according to the invention, i.e. 4-ethoxy-2-(piperazin-1-yl)-7-(pyridin-4-yl)-5H-pyrimido[5,4-b]indole, with fludarabine on the induction of apoptosis in B-CLL cells.

The FIG. 4 illustration exemplifies the synergistic effect of the substance according to the invention, i.e. 4-ethoxy-2-(piperazin-1-yl)-7-(pyridin-4-yl)-5H-pyrimido[5,4-b]indole, with fludarabine on the induction of apoptosis in B-CLL cells.

As shown, a combination of an exemplary substance according to the invention with fludarabine already yields a total toxicity of the B-CLL cells of over 80% with a 10% toxic concentration of each partner. In the case of an additive effect of both substances, only about 20% toxicity could be expected. If the concentration of both substances is increased such that each substance kills 20% of the cells in a separate test, a toxicity of almost 100% is obtained in this synergy experiment. This data proves that with a combined clinical treatment of fludarabine with one of the substances according to the invention the dosage could considerably be reduced thus minimizing or excluding possible undesired side-effects.

The invention claimed is:
1. A substituted 5H-pyramido[5,4-B]indole selected from the group consisting of:
  7-bromo-4-ethoxy-2-(piperazin-1-yl)-5H-pyrimido[5,4-b]indol-9-ol
  4-ethoxy-2-(piperazin-1-yl)-7-(pyridin-4-yl)-5H-pyrimido[5,4-b]indol-9-ol
  4-ethoxy-7-(3,4-dimethoxyphenyl)-2-(piperazin-1-yl)-5H-pyrimido[5,4-b]indol-9-ol
  7-(3,4-dimethoxyphenyl)-2-(piperazin-1-yl)-5H-pyrimido[5,4-b]indole-4,9-diol
  4-ethoxy-8-(3,4,5-trimethoxyphenyl)-2-(piperazin-1-yl)-5H-pyrimido[5,4-b]indole
  1-(7-(3,4-dimethoxyphenyl)-2-(piperazin-1-yl)-5H-pyrimido[5,4-b]indol-4-yl)piperidin-4-ol
  7-(3,4-dimethoxyphenyl)-2-(piperazin-1-yl)-5H-pyrimido[5,4-b]indol-4-ol
  4-((pyridin-2-yl)methoxy)-7-(3,4-dimethoxyphenyl)-2-(piperazin-1-yl)-5H-pyrimido[5,4-b]indole
  4-((pyridin-4-yl)methoxy)-7-(3,4-dimethoxyphenyl)-2-(piperazin-1-yl)-5H-pyrimido[5,4-b]indole
  4-((pyridin-3-yl)methoxy)-7-(3,4-dimethoxyphenyl)-2-(piperazin-1-yl)-5H-pyrimido[5,4-b]indole
  4-methylthio-2-(piperazin-1-yl)-7-(pyridin-4-yl)-5H-pyrimido[5,4-b]indole
  2-(7-(3,4-dimethoxyphenyl)-2-(piperazin-1-yl)-5H-pyrimido[5,4-b]indol-4-ylamino)ethanol
  7-bromo-2-(piperazin-1-yl)-5H-pyrimido[5,4-b]indol-4-ol
  4-(2-morpholinoethoxy)-7-(3,4-dimethoxyphenyl)-2-(piperazin-1-yl)-5H-pyrimido[5,4-b]indole
  7-(3,4-dimethoxyphenyl)-4-morpholino-2-(piperazin-1-yl)-5H-pyrimido[5,4-b]indole
  7-(3,4-dimethoxyphenyl)-2-(piperazin-1-yl)-4-thiomorpholino-5H-pyrimido[5,4-b]indole
  4-morpholino-2-(piperazin-1-yl)-7-(pyrindin-4-yl)-5H-pyrimido[5,4-b]indole
  7-(3,4-dimethoxyphenyl)-N-(2-morpholinoethyl)-2-(piperazin-1-yl)-5H-pyrimido[5,4-b]indole-4-amine
  7-(3,4-dimethoxyphenyl)-2-(piperazin-1-yl)-4-piperidino-5H-pyrimido[5,4-b]indole
  4-cyclopropylmethoxy-7-(3,4-dimethoxyphenyl)-2-(piperazin-1-yl)-5H-pyrimido[5,4-b]indole
  4-(1H-imidazol-1-yl)-7-(3,4-dimethoxyphenyl)-2-(piperazin-1-yl)-5H-pyrimido[5,4-b]indole
  7-(3,4-dimethoxyphenyl)-2-(piperazin-1-yl)-4-(piperidin-4-yloxy)-5H-pyrimido[5,4-b]indole
  4-cyclopropylmethoxy-2-(piperazin-1-yl)-7-(pyridin-4-yl)-5H-pyrimido[5,4-b]indole
  4-ethoxy-2-morpholino-7-(pyridin-4-yl)-5H-pyrimido[5,4-b]indole
  4-(4-ethoxy-2-(piperazin-1-yl)-5H-pyrimido[5,4-b]indol-7-yl)benzoic acid ethyl ester
  4-(4-ethoxy-2-(piperazin-1-yl)-5H-pyrimido[5,4-b]indol-7-yl)benzoic acid hydrochloride
  4-(4-ethoxy-2-(piperazin-1-yl)-5H-pyrimido[5,4-b]indol-7-yl)phenol hydrochloride
  3-(4-ethoxy-2-(piperazin-1-yl)-5H-pyrimido[5,4-b]indol-7-yl)benzoic acid methyl ester
  3-(4-ethoxy-2-(piperazin-1-yl)-5H-pyrimido[5,4-b]indol-7-yl)benzoic acid hydrochloride
  4-ethoxy-7-(furan-2-yl)-2-(piperazin-1-yl)-5H-pyrimido[5,4-b]indole
  tert-butyl-2-(4-ethoxy-2-(piperazin-1-yl)-5H-pyrimido[5,4-b]indol-7-yl)-1H-pyrrole-1-carboxylate
  tert-butyl-4-(4-ethoxy-7-(pyridin-3-yl)-5H-pyrimido[5,4-b]indol-2-yl)-piperazine-1-carboxylate
  7-(benzo[d][1,3]dioxol-5-yl)-4-ethoxy-2-(piperazin-1-yl)-5H-pyrimido[5,4-b]indole
  7-(3,4-dimethoxyphenyl)-2-(piperazin-1-yl)-N-(thiazol-2-yl)-5H-pyrimido[5,4-b]indole-4-amine
  7-(3,4-dimethoxyphenyl)-2-(piperazin-1-yl)-4-(1H-pyrrol-1-yl)-5H-pyrimido[5,4-b]indole
  7-(3,4-dimethoxyphenyl)-2-(piperazin-1-yl)-4-(1H-pyrazol-1-yl)-5H-pyrimido[5,4-b]indole
  7-(3,4-dimethoxyphenyl)-2-(piperazin-1-yl)-4-(1H-1,2,3-triazol-1-yl)-5H-pyrimido[5,4-b]indole
  7-(3,4-dimethoxyphenyl)-2-(piperazin-1-yl)-4-(4H-1,2,4-triazol-4-yl)-5H-pyrimido[5,4-b]indole
  7-(3,4-dimethoxyphenyl)-2-(piperazin-1-yl)-4-(pyrrolidin-1-yl)-5H-pyrimido[5,4-b]indole
  (4-(4-ethoxy-2-(piperazin-1-yl)-5H-pyrimido[5,4-b]indol-7-yl)piperazin-1-yl)(phenyl)methanone
  4-ethoxy-2-(piperazin-1-yl)-7-(4-(pyrimidin-2-yl)piperazin-1-yl)-5H-pyrimido[5,4-b]indole

4-ethoxy-2-(piperidin-4-yl)-7-(pyridin-4-yl)-5H-pyrimido[5,4-b]indole
4-ethoxy-7-(3,4-dimethoxyphenyl)-2-(piperidin-4-yl)-5H-pyrimido[5,4-b]indole
4-ethoxy-7-(3,4-dimethoxyphenyl)-2-(piperidin-3-yl)-5H-pyrimido[5,4-b]indole
4-ethoxy-7-(3,4-dimethoxyphenyl)-2-(pyridin-4-yl)-5H-pyrimido[5,4-b]indole
7-(3,4-dimethoxyphenyl)-2-(pyridin-4-yl)-5H-pyrimido[5,4-b]indol-4-ol
N,N-di-(2-hydroxyethyl)-4-ethoxy-7-(pyridin-4-yl)-5H-pyrimido[5,4-b]indole-2-amine
2-(4-ethoxy-9-methoxy-2-(piperazin-1-yl)-5H-pyrimido[5,4-b]indol-7-yl)benzeneamine
2-{2-(piperazin-1-yl)-7-(pyridin-4-yl)-5H-pyrimido[5,4-b]indol-4-yloxy}ethanol
2-ethoxy-4-(piperazin-1-yl)-7-(pyridin-4-yl)-5H-pyrimido[5,4-b]indole
4-ethoxy-2-(4-methylpiperazin-1-yl)-7-(pyridin-4-yl)-5H-pyrimido[5,4-b]indole
4-ethoxy-2-(piperazin-1-yl)-6-(pyridin-4-yl)-5H-pyrimido[5,4-b]indole
4-ethoxy-2-(piperazin-1-yl)-7-(2-aminopyridin-5-yl)-5H-pyrimido[5,4-b]indole
4-ethoxy-2-(piperazin-1-yl)-7-(3,4-dimethoxy-phenyl)-5H-pyrimido[5,4-b]indole
4-ethoxy-2-(piperazin-1-yl)-7-(pyridin-3-yl)-5H-pyrimido[5,4-b]indole
4-ethoxy-2-(piperazin-1-yl)-7-(pyridin-4-yl)-5H-pyrimido[5,4-b]indole
4-ethoxy-2-(piperazin-1-yl)-8-(pyridin-4-yl)-5H-pyrimido[5,4-b]indole
4-ethoxy-7-morpholino-2-(piperazin-1-yl)-5H-pyrimido[5,4-b]indole
4-ethoxy-9-methoxy-2-(piperazin-1-yl)-7-(pyridin-4-yl)-5H-pyrimido[5,4-b]indole.

2. Pharmaceutical composition comprising one or more compounds according to claim 1, and one or more ingredients selected from the group consisting of excipients and carriers.

3. Pharmaceutical composition according to claim 2, further comprising one or more of the following substances:
nucleoside analogues
alkylating agents
β₂ adrenoceptor agonists
disodium cromoglycate
corticosteroids
leukotriene antagonists
antihistamines
theophylline
PDE inhibitors
muscarine receptor antagonists
monoclonal antibodies against TNF-alpha or other active substances which inhibit the formation or release of TNF-alpha or the activity of TNF-alpha
monoclonal antibodies.

4. A method of treatment of leukemias and lymphomas, comprising administration of a substituted 5H-pyramido[5,4-B]indole selected from the group consisting of:
7-bromo-4-ethoxy-9-fluoro-2-(piperazin-1-yl)-5H-pyrimido[5,4-b]indole
7-bromo-9-chloro-4-ethoxy-2-(piperazin-1-yl)-5H-pyrimido[5,4-b]indole
7-bromo-4-ethoxy-2-(piperazin-1-yl)-5H-pyrimido[5,4-b]indol-9-ol
4-ethoxy-2-(piperazin-1-yl)-7-(pyridin-4-yl)-5H-pyrimido[5,4-b]indol-9-ol
4-ethoxy-7-(3,4-dimethoxyphenyl)-2-(piperazin-1-yl)-5H-pyrimido[5,4-b]indol-9-ol
7-(3,4-dimethoxyphenyl)-2-(piperazin-1-yl)-5H-pyrimido[5,4-b]indole-4,9-diol
4-ethoxy-8-(3,4,5-trimethoxyphenyl)-2-(piperazin-1-yl)-5H-pyrimido[5,4-b]indole
1-(7-(3,4-dimethoxyphenyl)-2-(piperazin-1-yl)-5H-pyrimido[5,4-b]indol-4-yl)piperidin-4-ol
7-(3,4-dimethoxyphenyl)-2-(piperazin-1-yl)-5H-pyrimido[5,4-b]indol-4-ol
4-((pyridin-2-yl)methoxy)-7-(3,4-dimethoxyphenyl)-2-(piperazin-1-yl)-5H-pyrimido[5,4-b]indole
4-((pyridin-4-yl)methoxy)-7-(3,4-dimethoxyphenyl)-2-(piperazin-1-yl)-5H-pyrimido[5,4-b]indole
4-((pyridin-3-yl)methoxy)-7-(3,4-dimethoxyphenyl)-2-(piperazin-1-yl)-5H-pyrimido[5,4-b]indole
4-methylthio-2-(piperazin-1-yl)-7-(pyridin-4-yl)-5H-pyrimido[5,4-b]indole
2-(7-(3,4-dimethoxyphenyl)-2-(piperazin-1-yl)-5H-pyrimido[5,4-b]indol-4-ylamino)ethanol
7-bromo-2-(piperazin-1-yl)-5H-pyrimido[5,4-b]indol-4-ol
4-(2-morpholinoethoxy)-7-(3,4-dimethoxyphenyl)-2-(piperazin-1-yl)-5H-pyrimido[5,4-b]indole
7-(3,4-dimethoxyphenyl)-4-morpholino-2-(piperazin-1-yl)-5H-pyrimido[5,4-b]indole
7-(3,4-dimethoxyphenyl)-2-(piperazin-1-yl)-4-thiomorpholino-5H-pyrimido[5,4-b]indole
4-morpholino-2-(piperazin-1-yl)-7-(pyrindin-4-yl)-5H-pyrimido[5,4-b]indole
7-(3,4-dimethoxyphenyl)-N-(2-morpholinoethyl)-2-(piperazin-1-yl)-5H-pyrimido[5,4-b]indole-4-amine
7-(3,4-dimethoxyphenyl)-2-(piperazin-1-yl)-4-piperidino-5H-pyrimido[5,4-b]indole
4-cyclopropylmethoxy-7-(3,4-dimethoxyphenyl)-2-(piperazin-1-yl)-5H-pyrimido[5,4-b]indole
4-(1H-imidazol-1-yl)-7-(3,4-dimethoxyphenyl)-2-(piperazin-1-yl)-5H-pyrimido[5,4-b]indole
7-(3,4-dimethoxyphenyl)-2-(piperazin-1-yl)-4-(piperidin-4-yloxy)-5H-pyrimido[5,4-b]indole
4-cyclopropylmethoxy-2-(piperazin-1-yl)-7-(pyridin-4-yl)-5H-pyrimido[5,4-b]indole
4-ethoxy-2-morpholino-7-(pyridin-4-yl)-5H-pyrimido[5,4-b]indole
4-(4-ethoxy-2-(piperazin-1-yl)-5H-pyrimido[5,4-b]indol-7-yl)benzoic acid ethyl ester
4-(4-ethoxy-2-(piperazin-1-yl)-5H-pyrimido[5,4-b]indol-7-yl)benzoic acid hydrochloride
4-(4-ethoxy-2-(piperazin-1-yl)-5H-pyrimido[5,4-b]indol-7-yl)phenol hydrochloride
3-(4-ethoxy-2-(piperazin-1-yl)-5H-pyrimido[5,4-b]indol-7-yl)benzoic acid methyl ester
3-(4-ethoxy-2-(piperazin-1-yl)-5H-pyrimido[5,4-b]indol-7-yl)benzoic acid hydrochloride
4-ethoxy-7-(furan-2-yl)-2-(piperazin-1-yl)-5H-pyrimido[5,4-b]indole
tert-butyl-2-(4-ethoxy-2-(piperazin-1-yl)-5H-pyrimido[5,4-b]indol-7-yl)-1H-pyrrole-1-carboxylate
tert-butyl-4-(4-ethoxy-7-(pyridin-3-yl)-5H-pyrimido[5,4-b]indol-2-yl)-piperazine-1-carboxylate
7-(benzo[d][1,3]dioxol-5-yl)-4-ethoxy-2-(piperazin-1-yl)-5H-pyrimido[5,4-b]indole
7-(3,4-dimethoxyphenyl)-2-(piperazin-1-yl)-N-(thiazol-2-yl)-5H-pyrimido[5,4-b]indole-4-amine
7-(3,4-dimethoxyphenyl)-2-(piperazin-1-yl)-4-(1H-pyrrol-1-yl)-5H-pyrimido[5,4-b]indole 7-(3,4-dimethoxyphenyl)-2-(piperazin-1-yl)-4-(1H-pyrazol-1-yl)-5H-pyrimido[5,4-b]indole 7-(3,4-dimethoxyphenyl)-2-(piperazin-1-yl)-4-(1H-1,2,3-triazol-1-yl)-5H-pyrimido[5,4-b]indole 7-(3,4-dimethoxyphenyl)-2-(piperazin-1-yl)-4-(4H-1,2,4-triazol-4-yl)-5H-pyrimido[5,4-b]indole 7-(3,4-dimethoxyphenyl)-2-(piperazin-1-yl)-4-(pyrrolidin-1-yl)-5H-pyrimido[5,4-b]indole (4-(4-ethoxy-2-(piperazin-1-yl)-5H-pyrimido[5,4-b]indol-7-yl)piperazin-1-yl)(phenyl)methanone 4-ethoxy-2-(piperazin-1-yl)-7-(4-(pyrimidin-2-yl)piperazin-1-yl)-5H-pyrimido[5,4-b]indole 4-ethoxy-2-(piperidin-4-yl)-7-(pyridin-4-yl)-5H-pyrimido[5,4-b]indole 4-ethoxy-7-(3,4-dimethoxyphenyl)-2-(piperidin-4-yl)-5H-pyrimido[5,4-b]indole 4-ethoxy-7-(3,4-dimethoxyphenyl)-2-(piperidin-3-yl)-5H-pyrimido[5,4-b]indole 4-ethoxy-7-(3,4-dimethoxyphenyl)-2-(pyridin-4-yl)-5H-pyrimido[5,4-b]indole 7-(3,4-dimethoxyphenyl)-2-(pyridin-4-yl)-5H-pyrimido[5,4-b]indol-4-ol N,N-di-(2-hydroxyethyl)-4-ethoxy-7-(pyridin-4-yl)-5H-pyrimido[5,4-b]indole-2-amine 2-(4-ethoxy-9-methoxy-2-(piperazin-1-yl)-5H-pyrimido[5,4-b]indol-7-yl)benzeneamine 2-{2-(piperazin-1-yl)-7-(pyridin-4-yl)-5H-pyrimido[5,4-b]indol-4-yloxy}ethanol 2-ethoxy-4-(piperazin-1-yl)-7-(pyridin-4-yl)-5H-pyrimido[5,4-b]indole 4-ethoxy-2-(4-methylpiperazin-1-yl)-7-(pyridin-4-yl)-5H-pyrimido[5,4-b]indole 4-ethoxy-2-(piperazin-1-yl)-6-(pyridin-4-yl)-5H-pyrimido[5,4-b]indole 4-ethoxy-2-(piperazin-1-yl)-7-(2-aminopyridin-5-yl)-5H-pyrimido[5,4-b]indole 4-ethoxy-2-(piperazin-1-yl)-7-(3,4-dimethoxy-phenyl)-5H-pyrimido[5,4-b]indole 4-ethoxy-2-(piperazin-1-yl)-7-(pyridin-3-yl)-5H-pyrimido[5,4-b]indole 4-ethoxy-2-(piperazin-1-yl)-7-(pyridin-4-yl)-5H-pyrimido[5,4-b]indole 4-ethoxy-2-(piperazin-1-yl)-8-(pyridin-4-yl)-5H-pyrimido[5,4-b]indole 4-ethoxy-7-morpholino-2-(piperazin-1-yl)-5H-pyrimido[5,4-b]indole 4-ethoxy-9-methoxy-2-(piperazin-1-yl)-7-(pyridin-4-yl)-5H-pyrimido[5,4-b]indole for the treatment of leukemias.

5. The method according to claim 4, for the treatment of chronic lymphatic B cell type leukemia.

6. The method according to claim 5, for the treatment of chronic lymphatic leukemia which is associated with an 11q chromosomal deletion.

7. A method of making compounds according to claim 1, the method comprising the following steps:

a) Reaction of the compounds of general formula I with phosgene derivatives in a solvent, to give the compounds of general formula II:

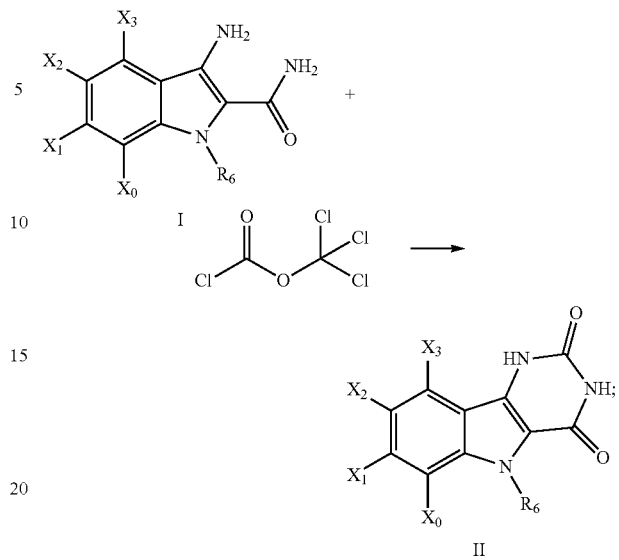

I b) Reaction of the compounds of general formula II with a halogenating agent, to give the compounds of general formula III:

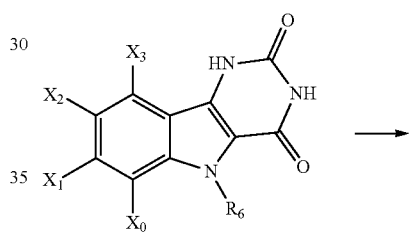

II c) Reaction of the compounds of general formula III with O, N, S or C nucleophiles, in alkanols or aprotic, dipolar solvents, to give the tricyclic compounds of general formula IV:

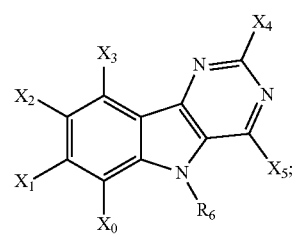

III

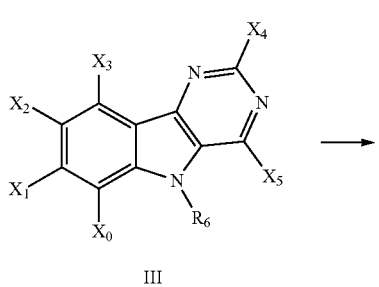

III

-continued

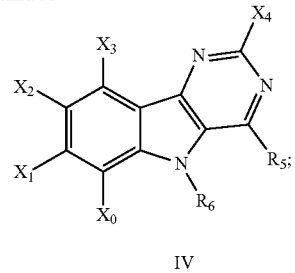

IV d) Reaction of the compounds of general formula IV with O, N, S or C nucleophiles, in a solvent, to give the compounds of general formula V:

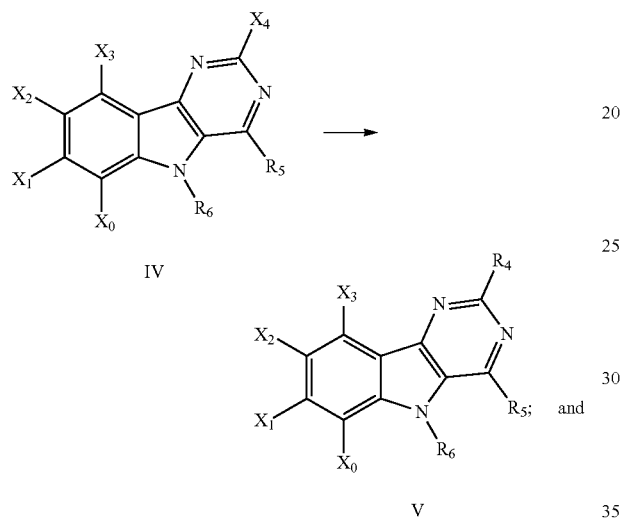

e) Reaction of the compounds of general formula V with O, N, S or C nucleophiles in a solvent, to give the compounds of general formula I:

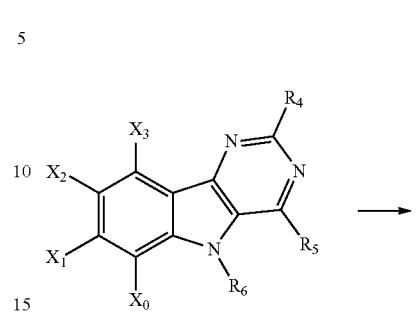

V

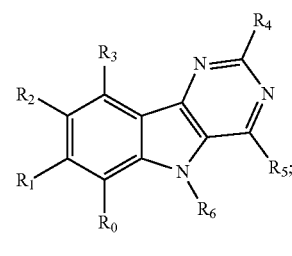

1 wherein $X_0$-$X_5$ are independently selected from F, Cl, Br, I, and H, wherein $X_4$ and $X_5$ are not H.

* * * * *

UNITED STATES PATENT AND TRADEMARK OFFICE
CERTIFICATE OF CORRECTION

PATENT NO.         : 8,664,233 B2
APPLICATION NO.    : 12/520480
DATED              : March 4, 2014
INVENTOR(S)        : Claudia Reichelt et al.

Page 1 of 1

It is certified that error appears in the above-identified patent and that said Letters Patent is hereby corrected as shown below:

In the Specification

In col. 5, at line 35, the third formula: " " should be: -- -- . 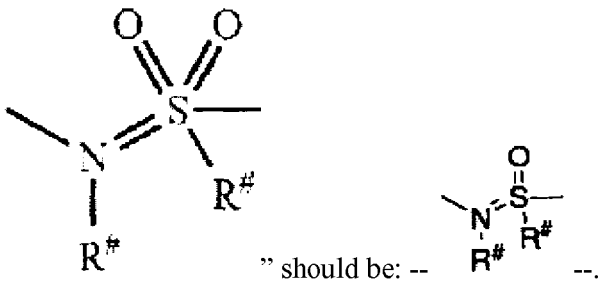

In col. 13, line 28, "...olopatadine theo-
                    phylline"

should be:
            --...olopatadine
            theophylline--.

In col. 19, the formula at lines 10-15: " 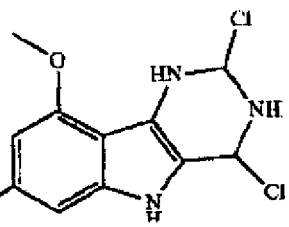 " should be:

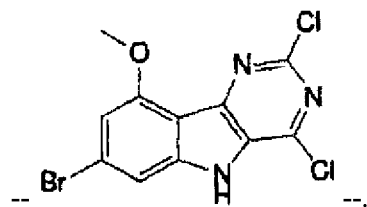 --.

Signed and Sealed this
First Day of July, 2014

Michelle K. Lee
*Deputy Director of the United States Patent and Trademark Office*